(12) United States Patent
Cushman et al.

(10) Patent No.: US 10,399,979 B2
(45) Date of Patent: Sep. 3, 2019

(54) JANUS KINASE INHIBITORS AND USES THEREOF

(71) Applicant: Purdue Research Foundation, West Lafayette, IN (US)

(72) Inventors: Mark Stanley Cushman, West Lafayette, IN (US); Mohamed S. A. Elsayed, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 16/175,915

(22) Filed: Oct. 31, 2018

(65) Prior Publication Data

US 2019/0127377 A1 May 2, 2019

Related U.S. Application Data

(60) Provisional application No. 62/579,327, filed on Oct. 31, 2017.

(51) Int. Cl.
| | | |
|---|---|---|
| *C07D 217/00* | (2006.01) | |
| *C07D 401/14* | (2006.01) | |
| *C07D 471/14* | (2006.01) | |
| *A61K 31/4745* | (2006.01) | |

(52) U.S. Cl.
CPC ........ *C07D 471/14* (2013.01); *A61K 31/4745* (2013.01)

(58) Field of Classification Search
CPC ............................ C07D 217/00; C07D 401/14
USPC ......................................................... 546/64
See application file for complete search history.

(56) References Cited

PUBLICATIONS

Nguyen et al., European Journal of Medicinal Chemistry (2014), 82, 363-371.*
Chaplin, D., "Overview of the Immune Response", J. Allergy Clin. Immunol. 2010, 125, pp. S3-23.
Cho, J., et al, "Heterogeneity of Autoimmune Diseases: Pathophysiologic Insights from Genetics and Implications for New Therapies", Nat. Med. 2015, 21, pp. 730-738.
Rawlings, J., et al, "The Jak/Stat Signaling Pathway", J. Cell Sci. 2004, 117, pp. 1281-1283.
Clark, J., et al, Discovery and Development of Janus Kinase (Jak) inhibitors for Inflammatory Diseases. J. Med. Chem. 2014, 57, pp. 5023-5038.
Furumoto, Y., et al, "The Arrival of Jak Inhibitors: Advancing the Treatment of Immune and Hematologic Disorders. BioDrugs : clinical immunotherapeutics, biopharmaceuticals and gene therapy", 2013, 27, pp. 431-438.
Yamaoka, K., "Janus Kinase Inhibitors for Rheumatoid Arthritis", Curr. Opin. Chem. Biol. 2016, 32, pp. 29-33.
Boyce, E., et al, "Impact of Tofacitinib on Patient Outcomes in Rheumatoid Arthritis—Review of Clinical Studies", Patient Related Outcome Measures 2016, 7, pp. 1-12.
Harris, C., "The Design and Application of Target-Focused Compound Libraries", Comb. Chem. High Throughput Screening 2011, 14, pp. 521-531.
Ferraccioli, R., "Synthesis of 6-Phenanthridinones and Their Heterocyclic Analogues through Palladium-Catalyzed Sequential Aryl-Aryl and N-Aryl Coupling", Org. Lett. 2004, 6, pp. 4759-4762.
Elsayed, M., et al, "Application of Sequential Palladium Catalysis for the Discovery of Janus Kinase Inhibitors in the Benzo[c]pyrrole[2,3-h][1,6]naphthyridine-5-one (BPM) Series" J. Med. Chem. 2018, 61, pp. 10440-10462.
Chen, Y., et al, "The JAK Inhibitor Antcin H Exhibits Direct Anticancer Activity while Enhancing Chemotherapy against LMP 1-Expressed Lymphoma" Leuk. Lymphoma 2019, 60, pp. 1193-1203.
Kontzias, A., et al, "Jakinibs: A New Class of Kinase Inhibitors in Cancer and Autoimmune Disease" Curr. Opin. Pharmacol. 2012, 12, pp. 464-470.
Atallah, E., et al, Prospect of JAK2 Inhibitor Therapy in Myeloproliferative Neoplasms: Expert Rev. Anticancer Ther. 2009, 9, pp. 663-670.
Bose, P., et al, "JAK2 Inhibitors for Myeloproliferative Neoplasms: What Is Next?" Blood 2017, 130, pp. 115-125.
Eghtedar, A., et al, "Phase 2 Study of the JAK Kinase Inhibitor Ruxolitinib in Patients with Refractory Leukemias, Including Postmyeloproliferative Neoplasm Acute Myeloid Leukemia" Blood 2012, 119, pp. 4614-4618.
Zhang, Q. et al. "Inhibition of mTORC1/2 Signaling Improves Anti-leukemic Efficacy of JAK/STAT Blockade in CRLF2 Rearranged and/or JAK Driven Philadelphia Chromosome-like Acute B-Cell Lymphoblastic Leukemia" Oncotarget 2018, 9, pp. 8027-8041.
Burger, R. et al, "Janus Kinase Inhibitor INCB20 Has Antiproliferative and Apoptotic Effects on Human Myeloma Cells In Vitro and In Vivo" Mol. Cancer Ther. 2009, 8, pp. 26-35.
Sonbol, M.,et al, "Comprehensive Review of JAK Inhibitors in Myeloproliferative Neoplasms" Ther. Adv. Hematol. 2013, 4, pp. 15-35.

* cited by examiner

*Primary Examiner* — Niloofar Rahmani
(74) *Attorney, Agent, or Firm* — Purdue Research Foundation; Liang Zeng Yan

(57) ABSTRACT

The invention described herein pertains to selective Janus kinase (JAK) inhibitors and methods of use thereof. Also described are methods for treating diseases involved abnormal JAK/STAT signaling pathway in mammals using the described selective JAK inhibitors or a pharmaceutical formulation thereof.

18 Claims, No Drawings

JANUS KINASE INHIBITORS AND USES THEREOF

CROSS-REFERENCE TO RELATED APPLICATIONS

The present U.S. patent application relates to and claims the priority benefit of U.S. Provisional Patent Application Ser. No. 62/579,327, filed Oct. 31, 2017, the content of which is hereby incorporated by reference in its entirety.

TECHNICAL FIELD

The present disclosure generally relates to novel therapeutic compounds, and in particular to selective Janus kinase (JAK) inhibitors and methods for treating diseases involved abnormal JAK/STAT signaling pathway in mammals using the described selective JAK inhibitors or a pharmaceutical formulation thereof.

BACKGROUND

This section introduces aspects that may help facilitate a better understanding of the disclosure. Accordingly, these statements are to be read in this light and are not to be understood as admissions about what is or is not prior art.

In humans, the immune response is a very complex process involved in defense against external pathogens or foreign tissues. Abnormalities in the human immune system often lead to disease states like cancer and autoimmune disorders (Chaplin, et al., *J. Allergy Clin. Immunol.* 2010, 125, S3-23; Cho, et al., *Nat. Med.* 2015, 21, 730-738). Autoimmune diseases are a group of diseases in which the immune system of an organism attacks body parts within the same organism. It is estimated that 24 million people are affected by autoimmune disease in the United States. Cytokines play essential roles in regulating the immune responses via cytokine-mediated gene activation or repression. The JAK-STAT pathway was discovered as a central player in the signal transduction cascade of many cytokines. Cytokine binding triggers receptor dimerization, which leads to JAK tyrosine kinase activation in which the two JAKs phosphorylate each other. JAK-mediated STAT phosphorylation subsequently induces dimerization of these signal transduction proteins and translocation to the nucleus, which initiates gene transcription (Rawlings, et al., *J. Cell Sci.* 2004, 117, 1281-1283). The JAK family has four members: JAK1, JAK2, JAK3 and TYK2. The JAKs are activated in specific patterns by different cytokines. JAK1 and JAK3 are activated by the members of the γ common (γc) subfamily, namely, interleukins IL-2, IL-4, IL-7, IL-9, IL-15, and IL-21 which can't activate JAK2 or TYK2. On the other hand, another subfamily of cytokines that contain the glycoprotein 130 (gp130) signal transducing subunit and includes IL-6, IL-11, IL-27, and several other cytokines that induce JAK1 activation, and JAK2 and TYK2 are also consistently engaged. Erythropoietin (EPO) receptors are another subfamily of homodimeric receptors that also includes the receptors for prolactin, thrombopoietin, and growth hormone. The EPO pathway activates JAK2 exclusively and is essential for erythropoiesis.

Since the discovery of the Janus family of kinases (JAKs) and their pivotal role in the immune system, they have attracted great interest for the development of new medications for various immune system-related disease. Over the past decade there have been extensive efforts to identify and design novel small-molecule JAK inhibitors with various profiles of subtype selectivity to address unmet medical needs such as transplant rejection, rheumatoid arthritis, cancers, and other autoimmune diseases (Clark, et al., *J. Med. Chem.* 2014, 57, 5023-5038). The selectivities of JAK inhibitors against the four family members and against other tyrosine kinases are very important. All of the current inhibitors are mixed inhibitors of all four kinases with varying potencies vs. each one (Furumoto, et al., *BioDrugs: clinical immunotherapeutics, biopharmaceuticals and gene therapy* 2013, 27, 431-438). Currently, two compounds have been approved by the FDA for the treatment of rheumatoid arthritis and organ transplant rejection, namely tofacitinib and ruxolitinib. These two compounds suffer from many side effects and more selective medications should be developed to overcome them (Yamaoka, et al., *Curr. Opin. Chem. Biol.* 2016, 32, 29-33; Boyce, et al., *Patient Related Outcome Measures* 2016, 7, 1-12). There are still unmet needs in those areas.

With regard to the design and synthesis of JAK inhibitors, it should be noted that Pd catalysis has offered new pathways for the preparation of pharmaceuticals. Tandem catalysis is a process in which the catalyst is used to catalyze more than one reaction for the construction of complex molecules from simple building blocks. In the present work, auto-tandem palladium catalysis was applied for the rapid construction of active JAK inhibitors with various selectivity and activities. This has made the synthesis of these compounds easier, it has allowed rapid diversification of newly designed scaffolds to obtain a wide range of activities and selectivity. Despite the extensive effort being made to discover safe and effective JAK kinases inhibitors, there is still a need for safer compounds with fewer side effects and higher selectivity. The rapid access to a focused library of active scaffolds will help to accelerate the identification of the best candidates for further development (Harris, et al., *Comb. Chem. High Throughput Screening* 2011, 14, 521-531).

BRIEF SUMMARY OF INVENTION

In some illustrative embodiments, the invention is related to a compound of formula (I)

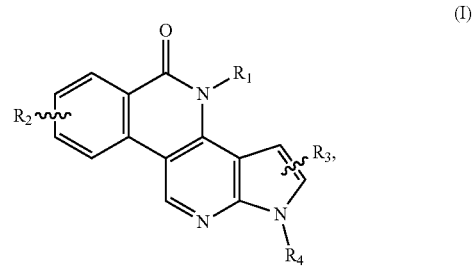

(I)

or a pharmaceutically acceptable salt, hydrate, or solvate thereof, wherein $R_1$ is an alkyl, alkenyl, heteroalkyl, heteroalkenyl, heterocyclyl, cycloalkyl, cycloalkenyl, cycloheteroalkyl, cycloheteroalkenyl, aryl, arylalkyl, and arylalkenyl, each of which is optionally substituted;

$R_2$ represent four substituents each independently selected from the group consisting of hydrogen, halo, azido, cyano, nitro, hydroxy, amino, thio, and derivatives thereof; or any two adjacent substituents that are taken together with the attached carbons to form an optionally substituted heterocycle, and each of other two substituents is defined as above;

$R_3$ represent two substituents each independently selected from the group consisting of hydrogen, halo, azido, cyano, nitro, hydroxy, amino, thio, and derivatives thereof; and $R_4$ is hydrogen, an alkyl, alkenyl, heteroalkyl, heteroalkenyl, heterocyclyl, cycloalkyl, cycloalkenyl, cycloheteroalkyl, cycloheteroalkenyl, aryl, arylalkyl, and arylalkenyl, each of which is optionally substituted.

In some other illustrative embodiments, the invention is related to a compound of formula (II)

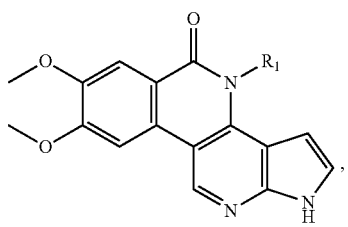

(II)

wherein $R_1$ is a $C_1$-$C_{12}$ alkyl, alkenyl, heteroalkyl, heteroalkenyl, heterocyclyl, cycloalkyl, cycloalkenyl, cycloheteroalkyl, cycloheteroalkenyl, aryl, arylalkyl, and arylalkenyl, each of which is optionally substituted.

In some illustrative embodiments, the invention is related to the following compounds:

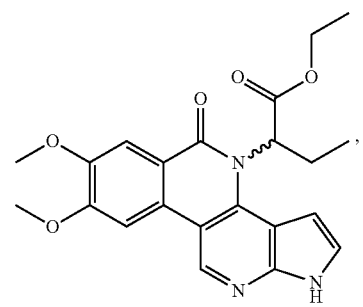

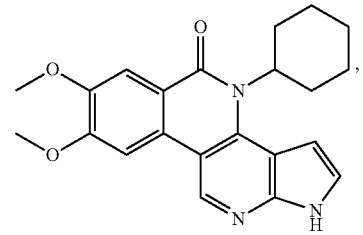

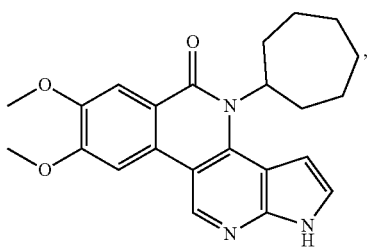

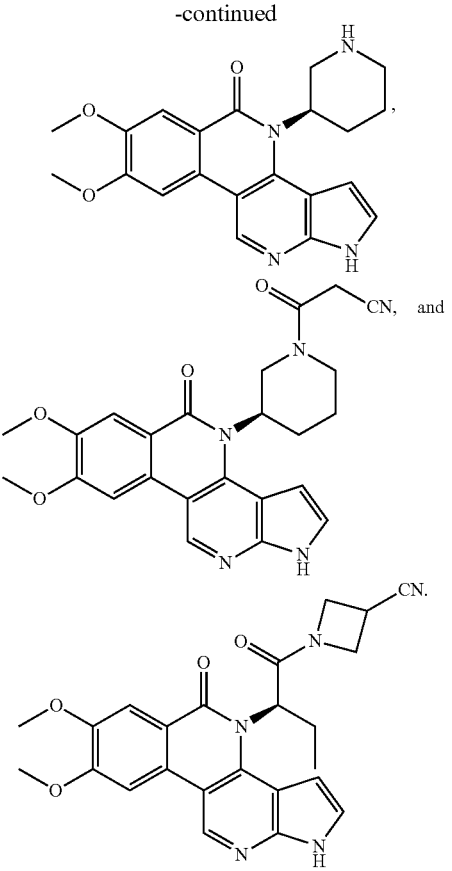

In some illustrative embodiments, the invention is related to a pharmaceutical composition comprising one or more compounds disclosed herein, or a pharmaceutically acceptable salt thereof, together with one or more diluents, excipients or carriers.

In some illustrative embodiments, the invention is related to a method for treating diseases mediated by abnormal JAK/STAT signaling pathway, such as inflammation, cancer, viral and bacterial infections, neurological and immunological disorders, comprising the step of administering a therapeutically effective amount of one or more compounds disclosed herein, and one or more carriers, diluents, or excipients, to a patient in need of relief from said disease.

In some illustrative embodiments, the invention is related to a method for treating diseases mediated by abnormal JAK/STAT signaling pathway, such as cancer, inflammation, viral and bacterial infections, neurological and immunological disorders, comprising the step of administering a therapeutically effective amount of one or more compounds of formula (I), and one or more carriers, diluents, or excipients, to a patient in need of relief from said disease:

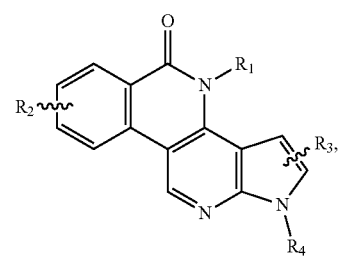

(I)

or a pharmaceutically acceptable salt, hydrate, or solvate thereof, wherein

R₁ is an alkyl, alkenyl, heteroalkyl, heteroalkenyl, heterocyclyl, cycloalkyl, cycloalkenyl, cycloheteroalkyl, cycloheteroalkenyl, aryl, arylalkyl, and arylalkenyl, each of which is optionally substituted;

R₂ represent four substituents each independently selected from the group consisting of hydrogen, halo, azido, cyano, nitro, hydroxy, amino, thio, and derivatives thereof; or any two adjacent substituents that are taken together with the attached carbons to form an optionally substituted heterocycle, and each of other two substituents is defined as above;

R₃ represent two substituents each independently selected from the group consisting of hydrogen, halo, azido, cyano, nitro, hydroxy, amino, thio, and derivatives thereof; and R₄ is hydrogen, an alkyl, alkenyl, heteroalkyl, heteroalkenyl, heterocyclyl, cycloalkyl, cycloalkenyl, cycloheteroalkyl, cycloheteroalkenyl, aryl, arylalkyl, and arylalkenyl, each of which is optionally substituted.

It is appreciated herein that the compounds described herein may be used alone or in combination with other compounds that may be therapeutically effective by the same or different modes of action. In addition, it is appreciated herein that the compounds described herein may be used in combination with other compounds that are administered to treat other symptoms of cancer, such as compounds administered to relieve pain, nausea, vomiting, and the like.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

In some illustrative embodiments, the invention is related to a compound having the formula (I)

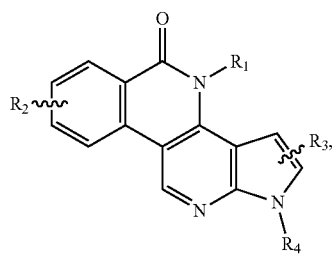

or a pharmaceutically acceptable salt thereof, wherein

R₁ is an alkyl, alkenyl, heteroalkyl, heteroalkenyl, heterocyclyl, cycloalkyl, cycloalkenyl, cycloheteroalkyl, cycloheteroalkenyl, aryl, arylalkyl, and arylalkenyl, each of which is optionally substituted;

R₂ represent four substituents each independently selected from the group consisting of hydrogen, halo, azido, cyano, nitro, hydroxy, amino, thio, and derivatives thereof; or any two adjacent substituents that are taken together with the attached carbons to form an optionally substituted heterocycle, and each of other two substituents is defined as above;

R₃ represent two substituents each independently selected from the group consisting of hydrogen, halo, azido, cyano, nitro, hydroxy, amino, thio, and derivatives thereof; and R₄ is hydrogen, an alkyl, alkenyl, heteroalkyl, heteroalkenyl, heterocyclyl, cycloalkyl, cycloalkenyl, cycloheteroalkyl, cycloheteroalkenyl, aryl, arylalkyl, and arylalkenyl, each of which is optionally substituted.

In some illustrative embodiments, the invention is related to a compound having the formula (I) as disclosed herein, wherein R₁ is a C3-C8 alkyl, alkenyl, cycloalkyl, cycloalkenyl, and heterocyclyl, each of which is optionally substituted.

In some illustrative embodiments, the invention is related to a compound having the formula (I) as disclosed herein, wherein R₁ is an optionally substituted C3-C8 cycloalkyl.

In some illustrative embodiments, the invention is related to a compound having the formula (I) as disclosed herein, wherein R₃ and R₄ are hydrogen.

In some other illustrative embodiments, the invention is related to a compound having formula (II),

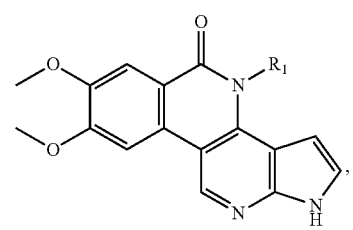

wherein R₁ is a C₁-C₁₂ alkyl, alkenyl, heteroalkyl, heteroalkenyl, heterocyclyl, cycloalkyl, cycloalkenyl, cycloheteroalkyl, cycloheteroalkenyl, aryl, arylalkyl, and arylalkenyl, each of which is optionally substituted.

In some other illustrative embodiments, the invention is related to a compound having formula (II), wherein R₁ is a C3-C8 alkyl, alkenyl, cycloalkyl, cycloalkenyl, and heterocyclyl, each of which is optionally substituted.

In some other illustrative embodiments, the invention is related to a compound having formula (II), wherein R₁ is an optionally substituted C3-C8 cycloalkyl.

In some illustrative embodiments, the invention is related to the following compounds:

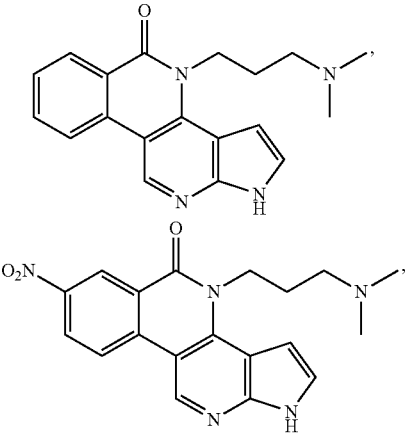

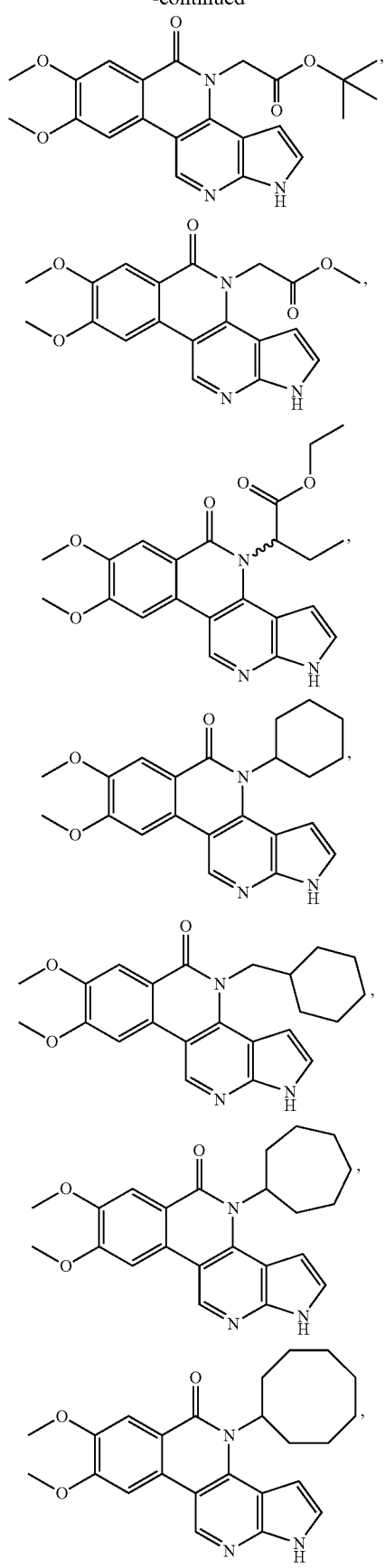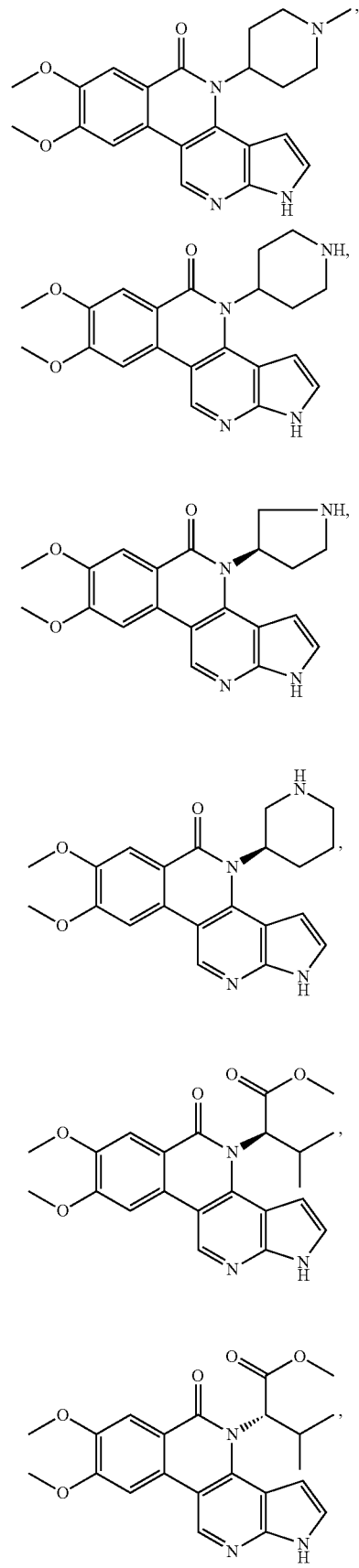

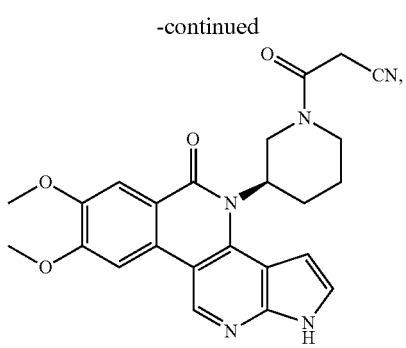

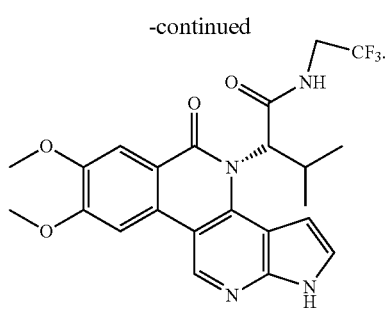

In some illustrative embodiments, the invention is related to a pharmaceutical composition comprising one or more compounds disclosed herein, or a pharmaceutically acceptable salt thereof, together with one or more diluents, excipients or carriers.

In some illustrative embodiments, the invention is related to a pharmaceutical composition comprising one or more compounds disclosed herein, or a pharmaceutically acceptable salt thereof, together with one or more diluents, excipients or carriers, for use in the treatment of cancer.

In some illustrative embodiments, the invention is related to a method for treating cancer comprising the step of administering a therapeutically effective amount of one or more compounds disclosed herein, and one or more carriers, diluents, or excipients, to a patient in need of relief from said cancer.

In some illustrative embodiments, the invention is related to a method for treating cancer comprising the step of administering a therapeutically effective amount of one or more compounds disclosed herein, in combination with one or more other compounds of the same or different mode of action, and one or more carriers, diluents, or excipients, to a patient in need of relief from said cancer.

In some illustrative embodiments, the invention is related to a method for treating diseases mediated by abnormal JAK/STAT pathway, such as inflammation, cancer, viral and bacterial infections, neurological and immunological disorders, comprising the step of administering a therapeutically effective amount of one or more compounds disclosed herein, and one or more carriers, diluents, or excipients, to a patient in need of relief from said disease.

In some illustrative embodiments, the invention is related to a method for treating diseases mediated by abnormal JAK/STAT pathway, such as inflammation, cancer, viral and bacterial infections, neurological and immunological disorders, comprising the step of administering a therapeutically effective amount of one or more compounds disclosed herein, in combination with one or more other compounds of the same or different mode of action, and one or more carriers, diluents, or excipients, to a patient in need of relief from said disease.

In some other illustrative embodiments, the invention is related to a method for treating diseases mediated by abnormal JAK/STAT signaling pathway, such as cancer, inflammation, viral and bacterial infections, neurological and immunological disorders, comprising the step of administering a therapeutically effective amount of one or more compounds of formula (I), and one or more carriers, diluents, or excipients, to a patient in need of relief from said disease:

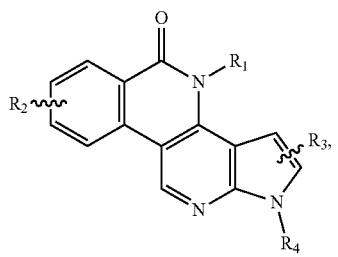

(I)

or a pharmaceutically acceptable salt, hydrate, or solvate thereof, wherein
- $R_1$ is an alkyl, alkenyl, heteroalkyl, heteroalkenyl, heterocyclyl, cycloalkyl, cycloalkenyl, cycloheteroalkyl, cycloheteroalkenyl, aryl, arylalkyl, and arylalkenyl, each of which is optionally substituted;
- $R_2$ represent four substituents each independently selected from the group consisting of hydrogen, halo, azido, cyano, nitro, hydroxy, amino, thio, and derivatives thereof; or any two adjacent substituents that are taken together with the attached carbons to form an optionally substituted heterocycle, and each of other two substituents is defined as above;
- $R_3$ represent two substituents each independently selected from the group consisting of hydrogen, halo, azido, cyano, nitro, hydroxy, amino, thio, and derivatives thereof; and
- $R_4$ is hydrogen, an alkyl, alkenyl, heteroalkyl, heteroalkenyl, heterocyclyl, cycloalkyl, cycloalkenyl, cycloheteroalkyl, cycloheteroalkenyl, aryl, arylalkyl, and arylalkenyl, each of which is optionally substituted.

In some other illustrative embodiments, the invention is related to a method for treating diseases mediated by abnormal JAK/STAT signaling pathway, such as cancer, inflammation, viral and bacterial infections, neurological and immunological disorders, comprising the step of administering a therapeutically effective amount of one or more compounds of formula (I) as disclosed herein, wherein $R_1$ is a C3-C8 alkyl, alkenyl, cycloalkyl, cycloalkenyl, and heterocyclyl, each of which is optionally substituted.

In some other illustrative embodiments, the invention is related to a method for treating diseases mediated by abnormal JAK/STAT signaling pathway, such as cancer, inflammation, viral and bacterial infections, neurological and immunological disorders, comprising the step of administering a therapeutically effective amount of one or more compounds of formula (I), wherein $R_1$ is an optionally substituted C3-C8 cycloalkyl.

In some other illustrative embodiments, the invention is related to a method for treating diseases mediated by abnormal JAK/STAT signaling pathway, such as cancer, inflammation, viral and bacterial infections, neurological and immunological disorders, comprising the step of administering a therapeutically effective amount of one or more compound having formula (I) as disclosed herein, wherein $R_3$ and $R_4$ are hydrogen.

In some other illustrative embodiments, the invention is related to a method for treating diseases mediated by abnormal JAK/STAT signaling pathway, such as cancer, inflammation, viral and bacterial infections, neurological and immunological disorders, comprising the step of administering a therapeutically effective amount of one or more compounds of the following compounds:

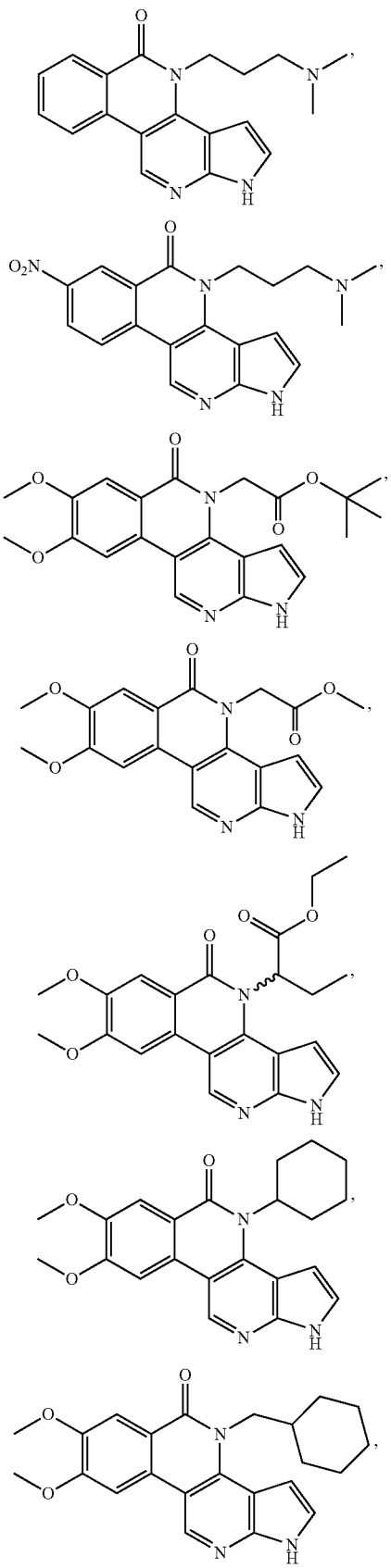

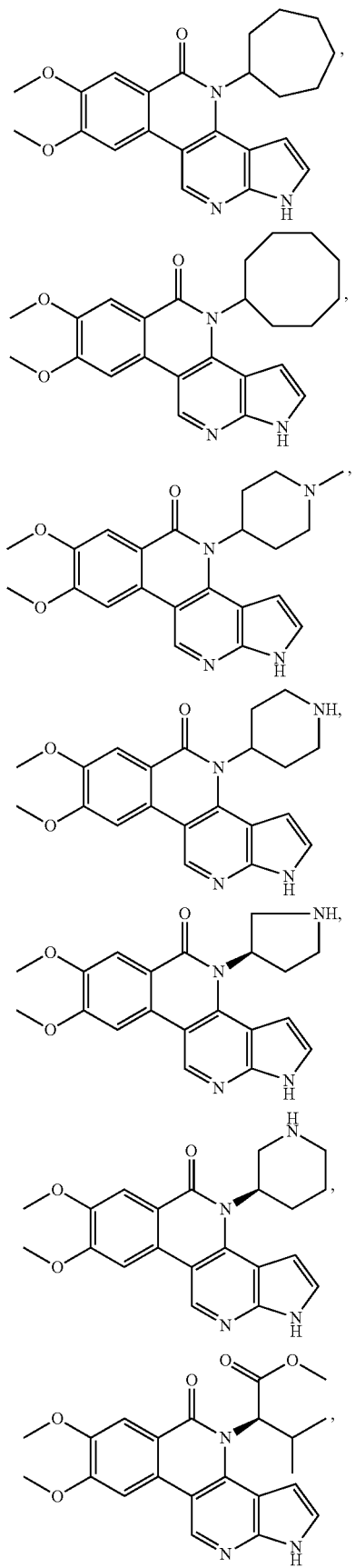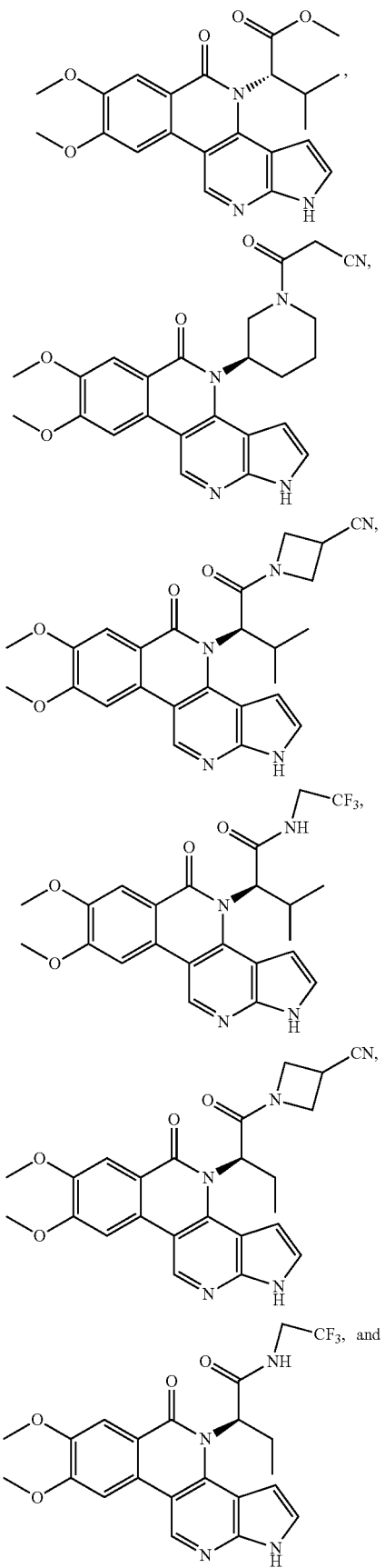

-continued

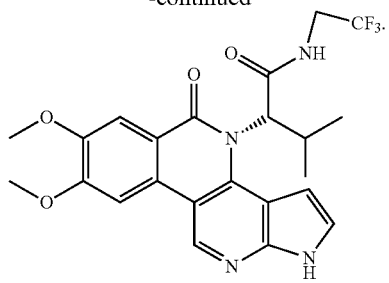

In another embodiment, pharmaceutical compositions containing one or more of the compounds are also described herein. In one aspect, the compositions include a therapeutically effective amount of the one or more compounds for treating a patient with cancer. It is to be understood that the compositions may include other component and/or ingredients, including, but not limited to, other therapeutically active compounds with the same or different modes of action, and one or more carriers, diluents, excipients, and the like. In another embodiment, methods for using the compounds and pharmaceutical compositions for treating patients with cancer are also described herein. In one aspect, the methods include the step of administering one or more of the compounds and/or compositions described herein to a patient with cancer. In another aspect, the methods include administering a therapeutically effective amount of the one or more compounds and/or compositions described herein for treating patients with cancer.

In addition, it is appreciated herein that the compounds described herein may be used in combination with other compounds that are administered to treat other symptoms of cancer, such as compounds administered to relieve pain, nausea, vomiting, and the like.

Unless defined otherwise, all technical and scientific terms used herein have the same meaning as commonly understood to one of ordinary skill in the art. As defined herein, the following terms and phrases shall have the meanings set forth below.

In the present disclosure the term "about" can allow for a degree of variability in a value or range, for example, within 10%, within 5%, or within 1% of a stated value or of a stated limit of a range. In the present disclosure the term "substantially" can allow for a degree of variability in a value or range, for example, within 90%, within 95%, 99%, 99.5%, 99.9%, 99.99%, or at least about 99.999% or more of a stated value or of a stated limit of a range.

The term "substituted" as used herein refers to a functional group in which one or more hydrogen atoms contained therein are replaced by one or more non-hydrogen atoms. The term "functional group" or "substituent" as used herein refers to a group that can be or is substituted onto a molecule. Examples of substituents or functional groups include, but are not limited to, a halogen (e.g., F, Cl, Br, and I); an oxygen atom in groups such as hydroxyl groups, alkoxy groups, aryloxy groups, aralkyloxy groups, oxo (carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, azides, hydroxylamines, cyano, nitro groups, N-oxides, hydrazides, and enamines; and other heteroatoms in various other groups.

The term "alkyl" as used herein refers to substituted or unsubstituted straight chain and branched alkyl groups and cycloalkyl groups having from 1 to about 20 carbon atoms ($C_1$-$C_{20}$), 1 to 12 carbons ($C_1$-$C_{12}$), 1 to 8 carbon atoms ($C_1$-$C_8$), or, in some embodiments, from 1 to 6 carbon atoms ($C_1$-$C_6$). Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "alkenyl" as used herein refers to substituted or unsubstituted straight chain and branched divalent alkenyl and cycloalkenyl groups having from 2 to 20 carbon atoms ($C_2$-$C_{20}$), 2 to 12 carbons ($C_2$-$C_{12}$), 2 to 8 carbon atoms ($C_2$-$C_8$) or, in some embodiments, from 2 to 4 carbon atoms ($C_2$-$C_4$) and at least one carbon-carbon double bond. Examples of straight chain alkenyl groups include those with from 2 to 8 carbon atoms such as —CH═CH—, —CH═CHCH$_2$—, and the like. Examples of branched alkenyl groups include, but are not limited to, —CH═C(CH$_3$)— and the like.

An alkynyl group is the fragment, containing an open point of attachment on a carbon atom that would form if a hydrogen atom bonded to a triply bonded carbon is removed from the molecule of an alkyne. The term "hydroxyalkyl" as used herein refers to alkyl groups as defined herein substituted with at least one hydroxyl (—OH) group.

The term "cycloalkyl" as used herein refers to substituted or unsubstituted cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. In some embodiments, cycloalkyl groups can have 3 to 6 carbon atoms ($C_3$-$C_6$). Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like.

The term "acyl" as used herein refers to a group containing a carbonyl moiety wherein the group is bonded via the carbonyl carbon atom. The carbonyl carbon atom is also bonded to another carbon atom, which can be part of a substituted or unsubstituted alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-40, 6-10, 1-5 or 2-5 additional carbon atoms bonded to the carbonyl group. An acryloyl group is an example of an acyl group. An acyl group can also include heteroatoms within the meaning here. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "aryl" as used herein refers to substituted or unsubstituted cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons ($C_6$-$C_{14}$) or from 6 to 10 carbon atoms ($C_6$-$C_{10}$) in the ring portions of the groups. Aryl groups can be unsubstituted or substituted, as defined herein. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed herein.

The term "aralkyl" and "arylalkyl" as used herein refers to alkyl groups as defined herein in which a hydrogen or carbon bond of an alkyl group is replaced with a bond to an aryl group as defined herein. Representative aralkyl groups include benzyl and phenylethyl groups and fused (cycloalkylaryl)alkyl groups such as 4-ethyl-indanyl. Aralkenyl groups are alkenyl groups as defined herein in which a hydrogen or carbon bond of an alkyl group is replaced with a bond to an aryl group as defined herein.

The term "heterocyclyl" as used herein refers to substituted or unsubstituted aromatic and non-aromatic ring compounds containing 3 or more ring members, of which, one or more is a heteroatom such as, but not limited to, B, N, O, and S. Thus, a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. In some embodiments, heterocyclyl groups include heterocyclyl groups that include 3 to 8 carbon atoms ($C_3$-$C_8$), 3 to 6 carbon atoms ($C_3$-$C_6$) or 6 to 8 carbon atoms ($C_6$-$C_8$).

A heteroaryl ring is an embodiment of a heterocyclyl group. The phrase "heterocyclyl group" includes fused ring species including those that include fused aromatic and non-aromatic groups. Representative heterocyclyl groups include, but are not limited to pyrrolidinyl, azetidinyl, piperidynyl, piperazinyl, morpholinyl, chromanyl, indolinonyl, isoindolinonyl, furanyl, pyrrolidinyl, pyridinyl, pyrazinyl, pyrimidinyl, triazinyl, thiophenyl, tetrahydrofuranyl, pyrrolyl, oxazolyl, oxadiazolyl, imidazolyl, triazyolyl, tetrazolyl, benzoxazolinyl, benzthiazolinyl, and benzimidazolinyl groups.

The term "heterocyclylalkyl" as used herein refers to alkyl groups as defined herein in which a hydrogen or carbon bond of an alkyl group as defined herein is replaced with a bond to a heterocyclyl group as defined herein. Representative heterocyclylalkyl groups include, but are not limited to, furan-2-yl methyl, furan-3-yl methyl, pyridine-3-yl methyl, tetrahydrofuran-2-yl methyl, and indol-2-yl propyl.

The term "heteroarylalkyl" as used herein refers to alkyl groups as defined herein in which a hydrogen or carbon bond of an alkyl group is replaced with a bond to a heteroaryl group as defined herein.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structure are substituted therewith.

The term "amine" as used herein refers to primary, secondary, and tertiary amines having, e.g., the formula N(group)$_3$ wherein each group can independently be H or non-H, such as alkyl, aryl, and the like. Amines include but are not limited to R—NH$_2$, for example, alkylamines, arylamines, alkylarylamines; R$_2$NH wherein each R is independently selected, such as dialkylamines, diarylamines, aralkylamines, heterocyclylamines and the like; and R$_3$N wherein each R is independently selected, such as trialkylamines, dialkylarylamines, alkyldiarylamines, triarylamines, and the like. The term "amine" also includes ammonium ions as used herein.

The term "amino group" as used herein refers to a substituent of the form —NH$_2$, —NHR, —NR$_2$, —NR$_3^+$, wherein each R is independently selected, and protonated forms of each, except for —NR$_3^+$, which cannot be protonated. Accordingly, any compound substituted with an amino group can be viewed as an amine. An "amino group" within the meaning herein can be a primary, secondary, tertiary, or quaternary amino group. An "alkylamino" group includes a monoalkylamino, dialkylamino, and trialkylamino group.

The terms "halo," "halogen," or "halide" group, as used herein, by themselves or as part of another substituent, mean, unless otherwise stated, a fluorine, chlorine, bromine, or iodine atom.

The term "haloalkyl" group, as used herein, includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, —CF(CH$_3$)$_2$ and the like.

The term "optionally substituted," or "optional substituents," as used herein, means that the groups in question are either unsubstituted or substituted with one or more of the substituents specified. When the groups in question are substituted with more than one substituent, the substituents may be the same or different. When using the terms "independently," "independently are," and "independently selected from" mean that the groups in question may be the same or different. Certain of the herein defined terms may occur more than once in the structure, and upon such occurrence each term shall be defined independently of the other.

The compounds described herein may contain one or more chiral centers, or may otherwise be capable of existing as multiple stereoisamers. It is to be understood that in one embodiment, the invention described herein is not limited to any particular stereochemical requirement, and that the compounds, and compositions, methods, uses, and medicaments that include them may be optically pure, or may be any of a variety of stereoisomeric mixtures, including racemic and other mixtures of enantiomers, other mixtures of diastereomers, and the like. It is also to be understood that such mixtures of stereoisomers may include a single stereochemical configuration at one or more chiral centers, while including mixtures of stereochemical configuration at one or more other chiral centers.

Similarly, the compounds described herein may include geometric centers, such as cis, trans, E, and Z double bonds. It is to be understood that in another embodiment, the invention described herein is not limited to any particular geometric isomer requirement, and that the compounds, and compositions, methods, uses, and medicaments that include them may be pure, or may be any of a variety of geometric isomer mixtures. It is also to be understood that such mixtures of geometric isomers may include a single configuration at one or more double bonds, while including mixtures of geometry at one or more other double bonds.

As used herein, the term "salts" and "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. Pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

Pharmaceutically acceptable salts can be synthesized from the parent compound which contains a basic or acidic moiety by conventional chemical methods. In some instances, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, the disclosure of which is hereby incorporated by reference.

The term "solvate" means a compound, or a salt thereof, that further includes a stoichiometric or non-stoichiometric amount of solvent bound by non-covalent intermolecular forces. Where the solvent is water, the solvate is a hydrate.

The term "prodrug" means a derivative of a compound that can hydrolyze, oxidize, or otherwise react under biological conditions (in vitro or in vivo) to provide an active compound, particularly a compound of the invention. Examples of prodrugs include, but are not limited to, derivatives and metabolites of a compound of the invention that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Specific prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger's Medicinal Chemistry and Drug Discovery 6th ed. (Donald J. Abraham ed., 2001, Wiley) and Design and Application of Prodrugs (H. Bundgaard ed., 1985, Harwood Academic Publishers GmbH).

Further, in each of the foregoing and following embodiments, it is to be understood that the formulae include and represent not only all pharmaceutically acceptable salts of the compounds, but also include any and all hydrates and/or solvates of the compound formulae or salts thereof. It is to be appreciated that certain functional groups, such as the hydroxy, amino, and like groups form complexes and/or coordination compounds with water and/or various solvents, in the various physical forms of the compounds. Accordingly, the above formulae are to be understood to include and represent those various hydrates and/or solvates. In each of the foregoing and following embodiments, it is also to be understood that the formulae include and represent each possible isomer, such as stereoisomers and geometric isomers, both individually and in any and all possible mixtures. In each of the foregoing and following embodiments, it is also to be understood that the formulae include and represent any and all crystalline forms, partially crystalline forms, and non-crystalline and/or amorphous forms of the compounds.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other nontoxic compatible substances employed in pharmaceutical formulations.

As used herein, the term "administering" includes all means of introducing the compounds and compositions described herein to the patient, including, but are not limited to, oral (po), intravenous (iv), intramuscular (im), subcutaneous (sc), transdermal, inhalation, buccal, ocular, sublingual, vaginal, rectal, and the like. The compounds and compositions described herein may be administered in unit dosage forms and/or formulations containing conventional nontoxic pharmaceutically acceptable carriers, adjuvants, and vehicles.

Illustrative formats for oral administration include tablets, capsules, elixirs, syrups, and the like. Illustrative routes for parenteral administration include intravenous, intraarterial, intraperitoneal, epidural, intraurethral, intrasternal, intramuscular and subcutaneous, as well as any other art recognized route of parenteral administration.

Illustrative means of parenteral administration include needle (including microneedle) injectors, needle-free injectors and infusion techniques, as well as any other means of parenteral administration recognized in the art. Parenteral formulations are typically aqueous solutions which may contain excipients such as salts, carbohydrates and buffering agents (preferably at a pH in the range from about 3 to about 9), but, for some applications, they may be more suitably formulated as a sterile non-aqueous solution or as a dried form to be used in conjunction with a suitable vehicle such as sterile, pyrogen-free water. The preparation of parenteral formulations under sterile conditions, for example, by lyophilization, may readily be accomplished using standard pharmaceutical techniques well known to those skilled in the art. Parenteral administration of a compound is illustratively performed in the form of saline solutions or with the compound incorporated into liposomes. In cases where the compound in itself is not sufficiently soluble to be dissolved, a solubilizer such as ethanol can be applied.

The dosage of each compound of the claimed combinations depends on several factors, including: the administration method, the condition to be treated, the severity of the condition, whether the condition is to be treated or prevented, and the age, weight, and health of the person to be treated. Additionally, pharmacogenomic (the effect of genotype on the pharmacokinetic, pharmacodynamic or efficacy profile of a therapeutic) information about a particular patient may affect the dosage used.

It is to be understood that in the methods described herein, the individual components of a co-administration, or combination can be administered by any suitable means, contemporaneously, simultaneously, sequentially, separately or in a single pharmaceutical formulation. Where the co-administered compounds or compositions are administered in separate dosage forms, the number of dosages administered per day for each compound may be the same or different. The compounds or compositions may be administered via the same or different routes of administration. The compounds or compositions may be administered according to simultaneous or alternating regimens, at the same or different times during the course of the therapy, concurrently in divided or single forms.

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill.

Depending upon the route of administration, a wide range of permissible dosages are contemplated herein, including doses falling in the range from about 1 μg/kg to about 1 g/kg. The dosages may be single or divided, and may administered according to a wide variety of protocols, including q.d. (once a day), b.i.d. (twice a day), t.i.d. (three times a day), or even every other day, once a week, once a month, once a quarter, and the like. In each of these cases it is understood that the therapeutically effective amounts described herein correspond to the instance of administration, or alternatively to the total daily, weekly, month, or quarterly dose, as determined by the dosing protocol.

In addition to the illustrative dosages and dosing protocols described herein, it is to be understood that an effective amount of any one or a mixture of the compounds described herein can be determined by the attending diagnostician or physician by the use of known techniques and/or by observing results obtained under analogous circumstances. In determining the effective amount or dose, a number of factors are considered by the attending diagnostician or physician, including, but not limited to the species of mammal, including human, its size, age, and general health, the specific disease or disorder involved, the degree of or involvement or the severity of the disease or disorder, the response of the individual patient, the particular compound administered, the mode of administration, the bioavailability characteristics of the preparation administered, the dose regimen selected, the use of concomitant medication, and other relevant circumstances.

The term "patient" includes human and non-human animals such as companion animals (dogs and cats and the like) and livestock animals. Livestock animals are animals raised for food production. The patient to be treated is preferably a mammal, in particular a human being.

The following non-limiting exemplary embodiments are included herein to further illustrate the invention. These exemplary embodiments are not intended and should not be interpreted to limit the scope of the invention in any way. It is also to be understood that numerous variations of these exemplary embodiments are contemplated herein.

Compound 1 has a conformationally rigid ring system that lowers the mobility of the side chain. Although the side chain of 1 is completely different from tofacitinib, compound 1 nevertheless has shown very high affinity for JAK2 and JAK3.

Initially, the synthetic pathway illustrated in Scheme 1 was investigated for the synthesis of compound 1 and two more analogs 7a and 7b with unsubstituted or with a nitro-substituted ring D. Compound 2 was protected using NaH in DMF with MOMCl. Buchwald chemistry was used to add the amine side chain to afford compound 4. The appropriate 2-bromo benzoic acid derivatives are commercially available and were used for the synthesis of compounds 5a-c. The acid was heated at reflux in SOCl$_2$ to obtain the acid chloride, which was reacted with compound 4 in methylene chloride and TEA. The intramolecular direct arylation reaction was used to obtain compounds 6a-c and the yield of this reaction was improved by replacing the cesium carbonate with potassium carbonate. Finally, compounds 1 and 7a-b were obtained by removing the MOM group by heating in concentrated HCl in THF.

Scheme 1

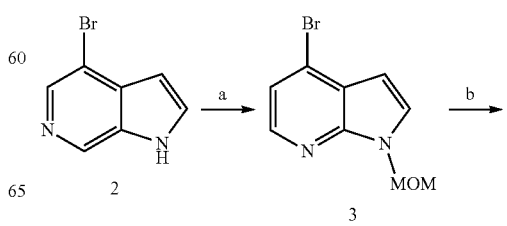

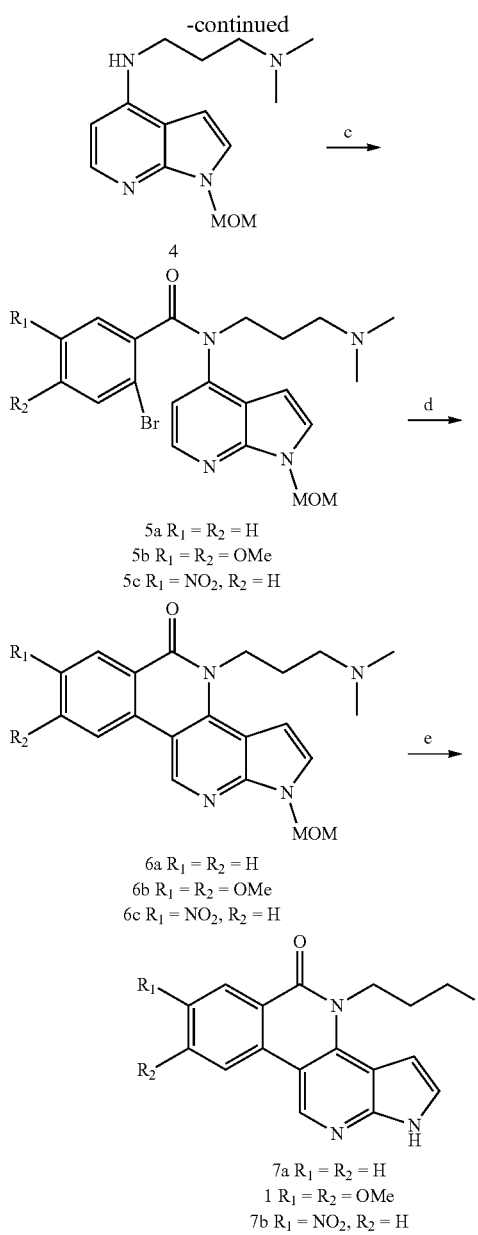

5a R$_1$ = R$_2$ = H
5b R$_1$ = R$_2$ = OMe
5c R$_1$ = NO$_2$, R$_2$ = H

6a R$_1$ = R$_2$ = H
6b R$_1$ = R$_2$ = OMe
6c R$_1$ = NO$_2$, R$_2$ = H

7a R$_1$ = R$_2$ = H
1 R$_1$ = R$_2$ = OMe
7b R$_1$ = NO$_2$, R$_2$ = H (a) MOMCl, BnBr or PMBCl, NaH, DMF, 0° C. to rt, 3 h;
(b) RNH$_2$, Pd$_2$(dba)$_3$, Xantphos, Cs$_2$CO$_3$, dioxane, 110° C., 16 h;
(c) ArCOCl, TEA, CH$_2$Cl$_2$, 0° C. to 60° C., 5 h;
(d) Pd(OAc)$_2$, K$_2$CO$_3$, Pcy$_3$, HBF$_4$, DMA, 130° C., 18 h;
(e) conc HCl, THF, 60° C., 20 h.

Focusing on the amine side chain, a literature search and molecular modeling study suggested that JAK inhibitor side chains are mainly hydrophobic because the pocket facing the side chain is predominantly formed of hydrophobic residues. The synthetic methodology used in Scheme 1 was not very useful for the synthesis of the second batch of compounds, because increasing the size of the amine substituents hindered amide formation with the acid chloride. Scheme 2 illustrates an alternate synthetic pathway used for the synthesis of compounds 13a-c. First, the protected azaindole compound 8 is converted to the amine 9 using Buchwald chemistry with benzophenone imine and palladium acetate. The amine 9 is reacted with 2-iodoacyl chloride derivatives to provide the common intermediate 10. The intermediate compound 10 is alkylated with various reactants using sodium hydride in DMF to afford compounds 11a-c. An intramolecular ring coupling reaction yields intermediates 12a-c, which can be easily deprotected by TFA to give the target compounds 13a-c.

The two schemes used for the synthesis of the target compounds were highly convergent but they were not successful in making compounds with bulkier side chains as, for example, a cyclohexyl group. In order to widen the range of side chains and facilitate scaffold decoration, a new tandem Pd reaction was engineered that can achieve the Buchwald amidation and the intramolecular arylation in just one step. Scheme 3 illustrates the new reaction and the versatility of side chain instillation that it provides. In this reaction, the amide 14a was reacted with the iodo compound 15 to generate compounds 16a in a single step instead of 4 steps in Scheme 1. The amides 14a can be easily obtained from the commercially available o-bromo acids and compound 15 is prepared from commercially available 4-iodo-7-azaindole.

The reaction is a modification of the Catellani reaction, in which the bifunctionalization of aryl halide is facilitated with norborene. The original conditions reported by Catellani and coworkers didn't provide the required compound in a good yield (Ferraccioli et al., *Org. Lett.* 2004, 6, 4759-4762). The aryl iodide in the present case is different from o-iodotoluene in the original paper. In addition to optimizing the yield, the versatility of the reaction needed to be augmented in order to facilitate the synthesis of a broad range of JAK inhibitors. The conditions of the Catellani reaction were optimized as shown in Table 1.

Scheme 2

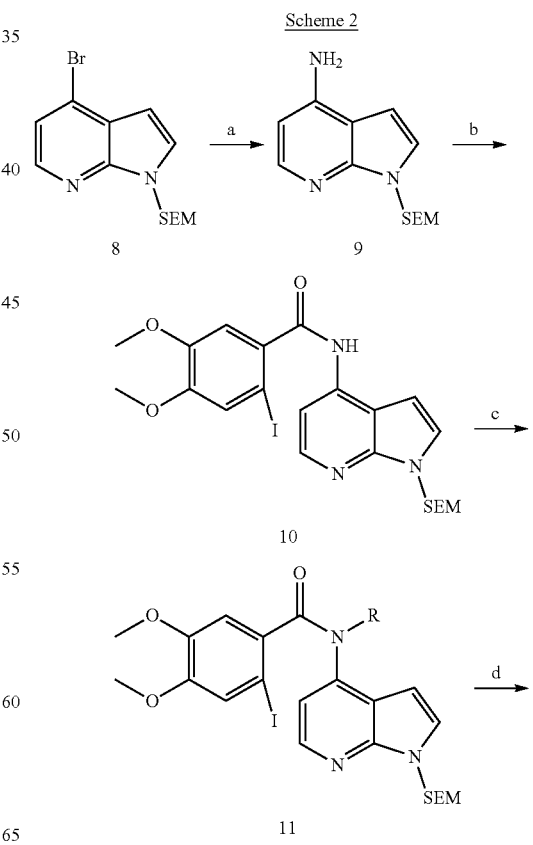

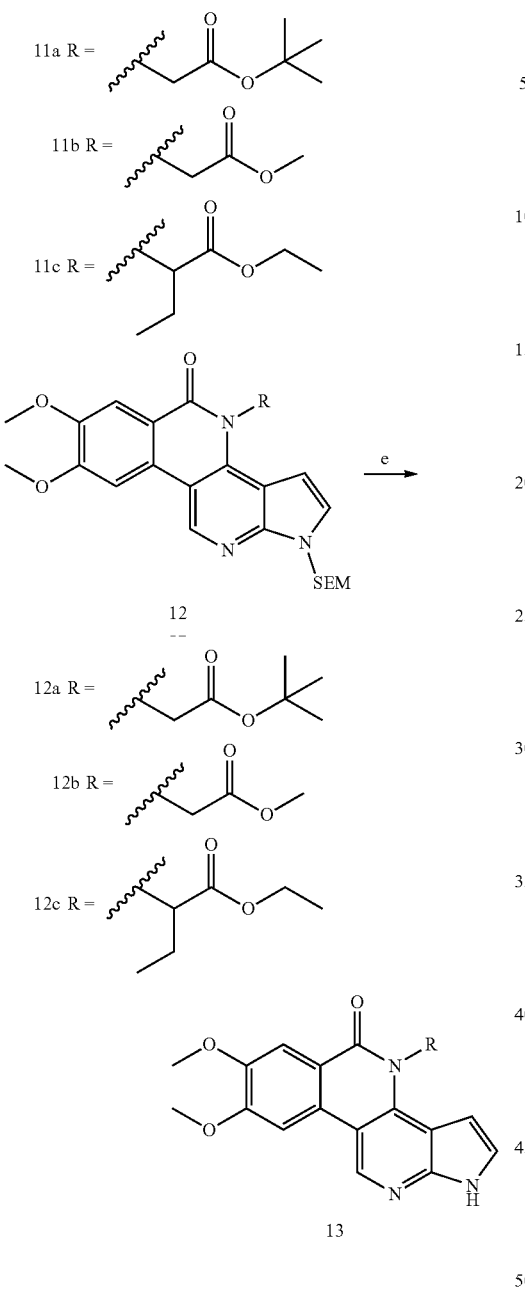

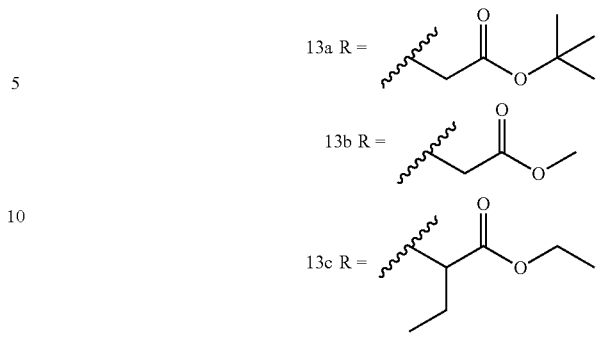

a) i) Pd(OAc)₂, benzophenone imine, Cs₂CO₃, xantphos, dioxane, 110° C.;
ii) NH₂OH·HCl, NaOAc, MeOH, rt;
b) ArCOCl, TEA, CH₂Cl₂, rt, 16 h.
c) R—Br, NaH, DMF, rt, 18 h;
d) Pd(OAc)₂, PCy₃, HBF₄, K₂CO₃, DMA, 130° C., 18 h;
e) i) TFA, CH₂Cl₂, ii) ethylenediamine, NaOH, MeOH.

Scheme 3 (see Table 1 for detailed reaction conditions)

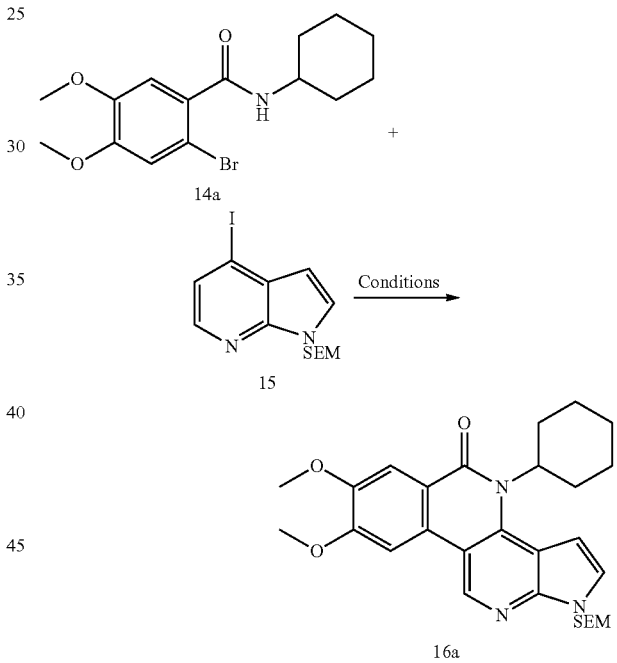

TABLE 1

Optimization of the Catellani reaction.

| Entry* | Catalyst | Ligand | Base | Solvent | Additive | Temp (C.°)/time (h) | Yield %[a] |
|---|---|---|---|---|---|---|---|
| 1 | Pd(OAc)₂ | TFP[b] | K₂CO₃ | CH₃CN | — | 85/18 | <2 |
| 2 | Pd(OAc)₂ | TFP | K₂CO₃ | DMF | — | 105/18 | 0 |
| 3 | Pd(OAc)₂ | TFP | K₂CO₃ | CH₃CN | Norborene | 100/18 | 20 |
| 4 | Pd(OAc)₂ | PPh₃ | K₂CO₃ | DMA | Norborene | 130/18 | 4 |
| 5 | Pd(OAc)₂ | TFP | Cs₂CO₃ | CH₃CN | Norborene | 85/18 | 24 |
| 6 | Pd(OAc)₂ | TFP | Cs₂CO₃ | dioxane | Norborene | 95/18 | 21 |
| 7 | Pd(OAc)₂ | TFP | Cs₂CO₃ | THF | Norborene | 70/18 | 34 |
| 8 | Pd(OAc)₂ | TFP | t-BuOK | Toluene | Norborene | 100/18 | 56 |
| 9 | Pd(OAc)₂ | TFP | Cs₂CO₃ | Toluene | Norborene | 100/18 | 68 |
| 10 | Pd(OAc)₂ | TFP | t-BuOK | Tol/CH₃CN | Norborene | 100/18 | 68 |

TABLE 1-continued

Optimization of the Catellani reaction.

| Entry* | Catalyst | Ligand | Base | Solvent | Additive | Temp (C.°)/time (h) | Yield %[a] |
|---|---|---|---|---|---|---|---|
| 11 | Pd(OAc)$_2$ | xantphos | Cs$_2$CO$_3$ | Tol/CH$_3$CN | Norborene | 100/18 | 52 |
| 12 | Pd(OAc)$_2$ | PCy$_3$•HB$_4$ | Cs$_2$CO$_3$ | Tol/CH$_3$CN | Norborene | 100/18 | 42 |
| 13 | Pd(OAc)$_2$ | S-Phos | Cs$_2$CO$_3$ | Tol/CH$_3$CN | Norborene | 100/18 | 32 |
| 14 | Pd$_2$(dba)$_3$ | TFP | Cs$_2$CO$_3$ | Toluene | Norborene | 100/18 | 70 |
| 15 | Pd(OTFA)$_2$ | TFP | Na$_2$CO$_3$ | Toluene | Norborene | 100/8 | 75 |
| 16 | Pd(OTFA)$_2$ | TFP | Cs$_2$CO$_3$ | Toluene | Norborene | 100/20 | 78 |

[a] all the numbers are the isolated yields,
[b] Tr(2-Furyl)phosphine

Changing the solvent from acetonitrile to dioxane or DMA (entry 4 of Table 1) was not optimal for the reaction. Further investigation revealed that toluene was the best solvent (entry 9 of Table 1). The use of Potassium carbonate as a base proved to be ineffective. After some trials, cesium carbonate was established to be the best base for the reaction. Any ligand other than TFP [tri(2-furyl)phosphine] decreased the yield of the reaction. Finally, palladium acetate was replaced with palladium trifluroracetate and this enhanced the yield as expected with a pyrrolopyridine scaffold because the palladium center is more cationic.

After the optimization of the reaction conditions, the reaction was employed for the synthesis of the target compounds 17a-m. Scheme 5 illustrates the substrate scope and the target compounds that were synthesized using the optimized reaction condition. Compounds 16a-l were deprotected using TFA and ethylenediamine.

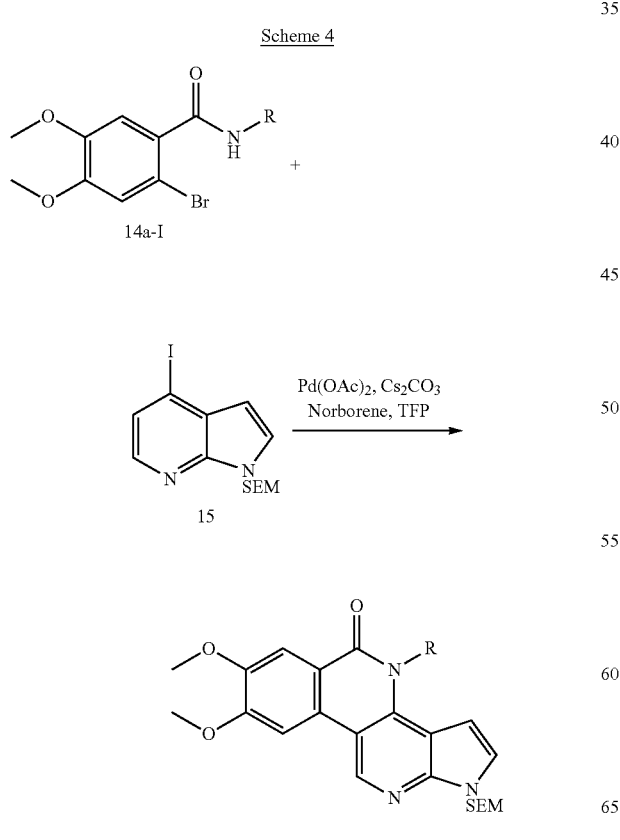

Scheme 4

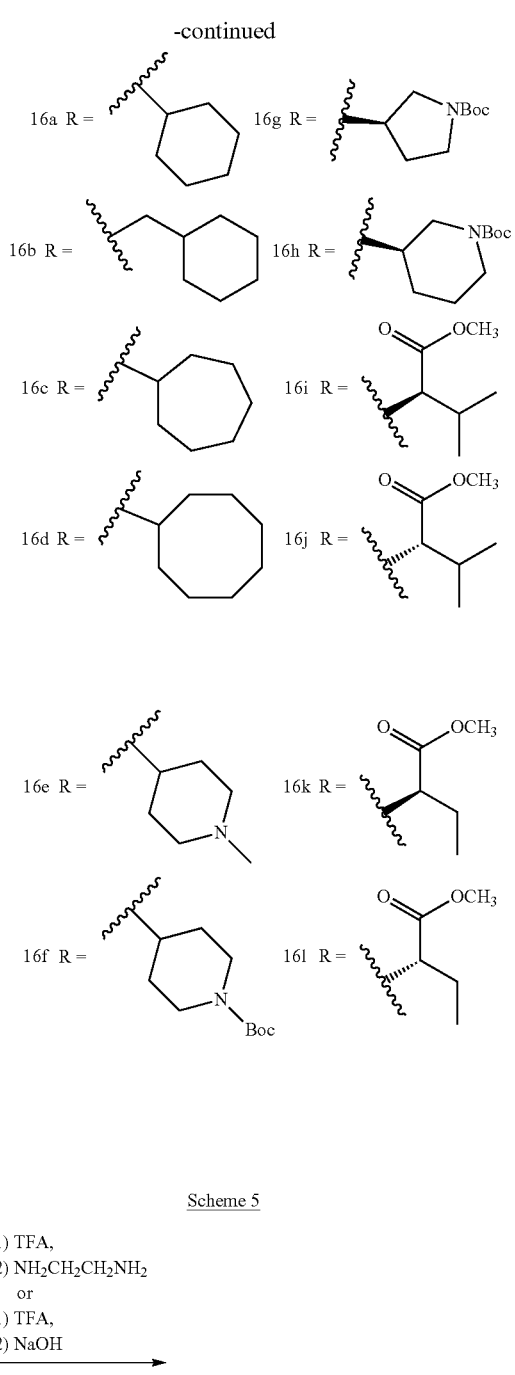

Scheme 5

1) TFA,
2) NH$_2$CH$_2$CH$_2$NH$_2$
or
1) TFA,
2) NaOH 16a-l →

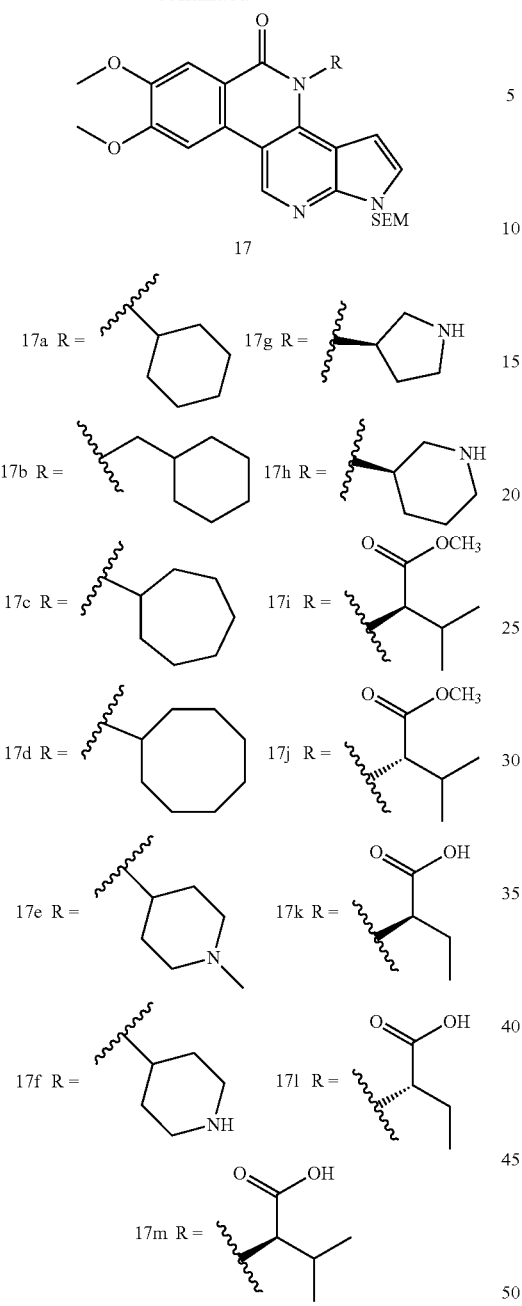
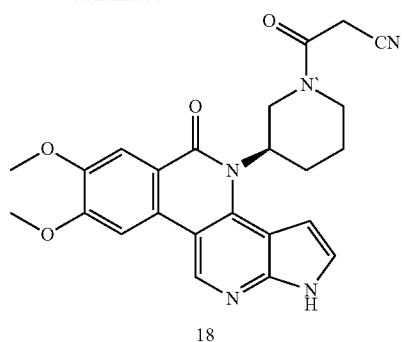
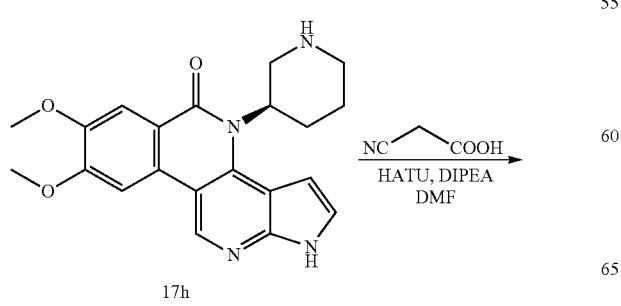
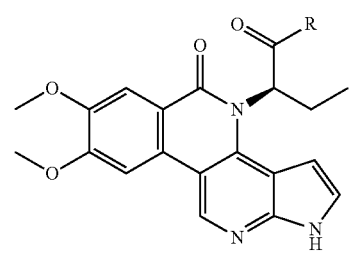
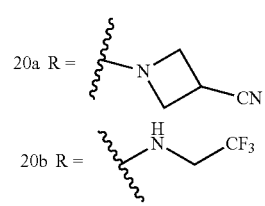

-continued

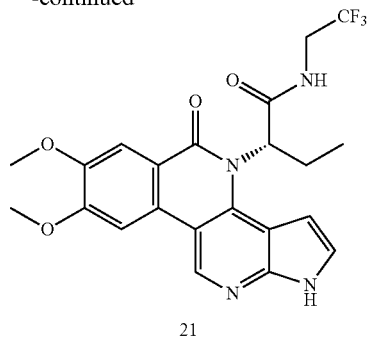

21

The target compounds 18, 19a,b, 20a,b and 21 were synthesized from the corresponding amines or acids by coupling reaction using HATU in DMF (Schemes 6 and 7).

JAK Inhibition Activity Assays and Results

Reagents used in JAK inhibition assay: Base Reaction buffer; 20 mM Hepes (pH 7.5), 10 mM MgCl2, 1 mM EGTA, 0.02% Brij35, 0.02 mg/ml BSA, 0.1 mM Na3VO4, 2 mM DTT, 1% DMSO. Required cofactors are added individually to each kinase reaction. Assays were carried out according to vendor's specifications as followings:

Prepare indicated substrate in freshly prepared Base Reaction Buffer

Deliver any required cofactors to the substrate solution above

Deliver indicated kinase into the substrate solution and gently mix

Deliver compounds in DMSO into the kinase reaction mixture by Acoustic technology (Echo550; nanoliter range), incubate for 20 minutes at room temperature Deliver 33P-ATP (specific activity 10 µCi/µl) into the reaction mixture to initiate the reaction.

Incubate kinase reaction for 2 hours at room temperature

Reactions are spotted onto P81 ion exchange paper

Detect kinase activity by filter-binding method.

The JAK inhibition assay results for all of the compounds are shown in Table 2.

TABLE 2

Enzyme assay results of the synthesized compounds.

| Compound ID: | JAK-1 $IC_{50}$ (nM) | JAK-2 $IC_{50}$ (nM) | JAK-3 $IC_{50}$ (nM) | TYK-2 $IC_{50}$ (nM) |
|---|---|---|---|---|
| Tofacitinib | 1.4215 ± 0.0655 | 1.0856 ± 0.1684 | 0.24065 ± 0.00185 | 10.38 ± 0.85 |
| 1 | 95.62 ± 5.18 | 72.97 ± 2.35 | 129.75 ± 0.45 | 427.45 ± 11.45 |
| 7a | 423.8 ± 4.1 | 229.25 ± 8.45 | 285.9 ± 8.5 | 708.65 ± 34.35 |

TABLE 2-continued
Enzyme assay results of the synthesized compounds.
| Compound ID: | JAK-1 IC$_{50}$ (nM) | JAK-2 IC$_{50}$ (nM) | JAK-3 IC$_{50}$ (nM) | TYK-2 IC$_{50}$ (nM) |
|---|---|---|---|---|
| 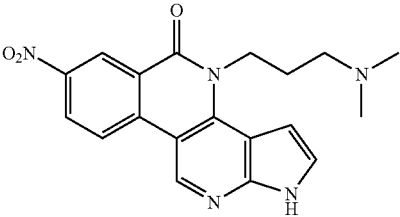 [SMILES: CN(C)CCCn1c(=O)c2cc([N+](=O)[O-])ccc2c2cnc3[nH]ccc3c21] 7b | 3334 ± 30 | 489.65 ± 2.15 | 1111.5 ± 53.5 | 4766 ± 207 |
| 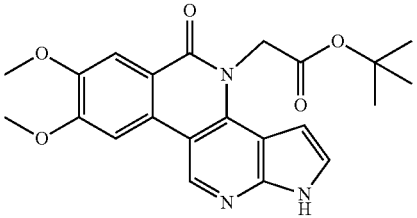 [SMILES: COc1cc2c(=O)n(CC(=O)OC(C)(C)C)c3c4cc[nH]c4ncc3c2cc1OC] 13a | 103.15 ± 1.25 | 14.115 ± 0.945 | 9.939 ± 0.091 | >100 |
| 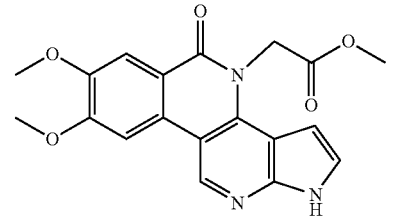 13b | 9.885 ± 1.1815 | 17.555 ± 0.075 | 6.6535 ± 0.0525 | 18.42 ± 1.05 |
| 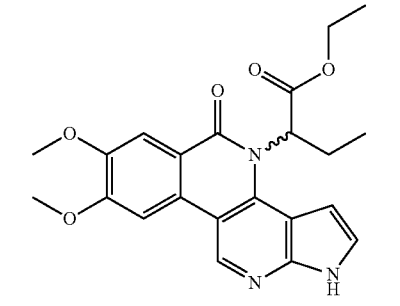 [SMILES: CCOC(=O)C(CC)n1c(=O)c2cc(OC)c(OC)cc2c2cnc3[nH]ccc3c21] 13c | 1.91 ± 0.09 | 10.44 ± 0.41 | 27.5 ± 0.75 | 17.4 ± 0.88 |
| 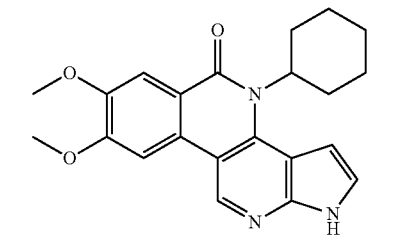 [SMILES: COc1cc2c(=O)n(C3CCCCC3)c3c4cc[nH]c4ncc3c2cc1OC] 17a | 4.23 ± 0.34 | 1.07 ± 0.05 | 2.92 ± 0.14 | 1.93 ± 0.07 |

TABLE 2-continued
Enzyme assay results of the synthesized compounds.
| Compound ID: | JAK-1 IC$_{50}$ (nM) | JAK-2 IC$_{50}$ (nM) | JAK-3 IC$_{50}$ (nM) | TYK-2 IC$_{50}$ (nM) |
|---|---|---|---|---|
| 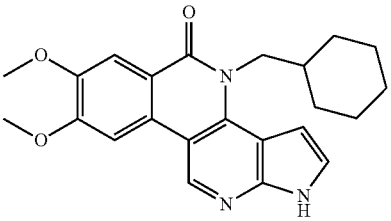 [SMILES: COc1cc2c(=O)n(CC3CCCCC3)c3c4cc[nH]c4ncc3c2cc1OC] 17b | 125.1 ± 3.6 | 3.57 ± 0.02 | 1.65 ± 0.1 | 39.43 ± 3.95 |
| 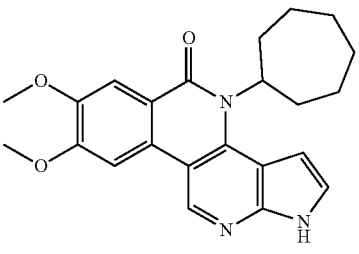 [SMILES: COc1cc2c(=O)n(C3CCCCCC3)c3c4cc[nH]c4ncc3c2cc1OC] 17c | 6.59 ± 0.48 | 0.89 ± 0.09 | 1.09 ± 0.03 | 2.24 ± 0.30 |
| 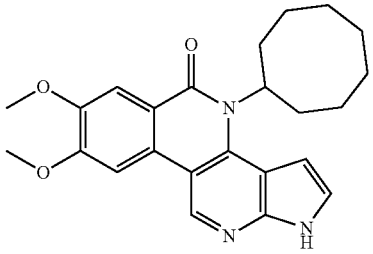 [SMILES: COc1cc2c(=O)n(C3CCCCCCC3)c3c4cc[nH]c4ncc3c2cc1OC] 17d | 17.86 ± 0.97 | 1.81 ± 0.003 | 1.01 ± 0.02615 | 8.38 ± 0.44 |
| 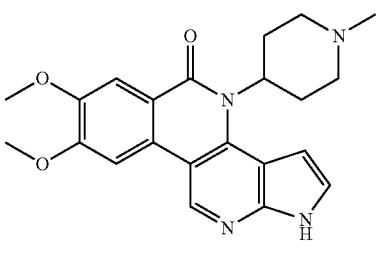 17e | 37.54 ± 1.08 | 37.07 ± 1.55 | 124.1 ± 7.1 | 166.85 ± 36.35 |
| 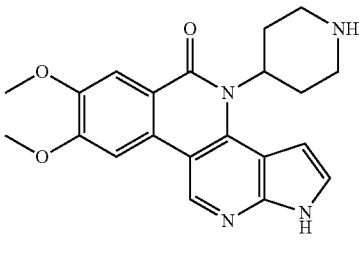 [SMILES: COc1cc2c(=O)n(C3CCNCC3)c3c4cc[nH]c4ncc3c2cc1OC] 17f | 11.48 ± 0.61 | 14.70 ± 0.12 | 18.31 ± 0.09 | 32.39 ± 3.61 |

TABLE 2-continued
Enzyme assay results of the synthesized compounds.
| Compound ID: | JAK-1 IC$_{50}$ (nM) | JAK-2 IC$_{50}$ (nM) | JAK-3 IC$_{50}$ (nM) | TYK-2 IC$_{50}$ (nM) |
|---|---|---|---|---|
| 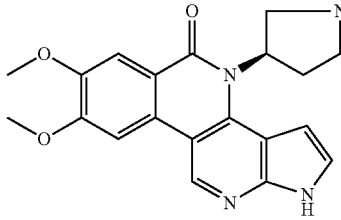<br>17g | 10.61 ± 0.22 | 37.91 ± 2.60 | 143.7 ± 1.3 | 176.3 ± 2.3 |
| 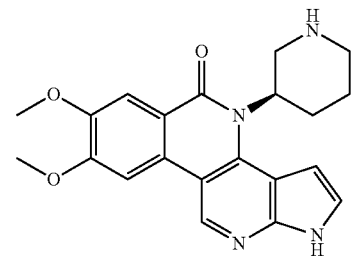 [SMILES: COc1cc2c(=O)n([C@@H]3CCCNC3)c3c4cc[nH]c4ncc3c2cc1OC]<br>17h | 5.28 ± 0.19 | 8.91 ± 0.29 | 23.45 ± 0.11 | 45.10 ± 4.8 |
| 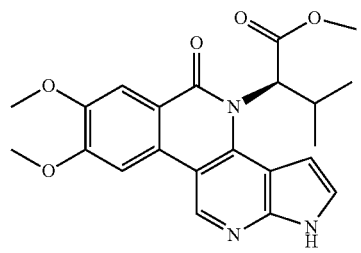<br>17i | 58.26 ± 1.92 | 63.04 ± 1.69 | 28.94 ± 1.55 | 256.5 ± 16.5 |
| 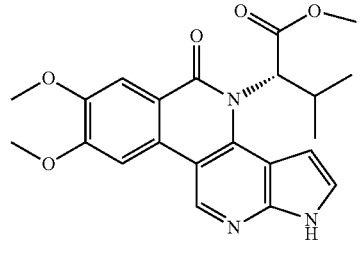<br>17j | 304.45 ± 38.05 | 220.8 ± 16.3 | 95.56 ± 1.74 | 1502 ± 124 |
| 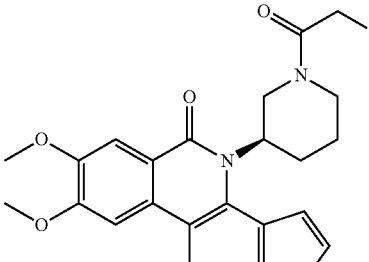<br>18 | 1.02 ± 0.22 | 3.12 ± 0.05 | 2.55 ± 0.02 | 4.35 ± 0.38 |

TABLE 2-continued
Enzyme assay results of the synthesized compounds.
| Compound ID: | JAK-1 IC$_{50}$ (nM) | JAK-2 IC$_{50}$ (nM) | JAK-3 IC$_{50}$ (nM) | TYK-2 IC$_{50}$ (nM) |
|---|---|---|---|---|
| 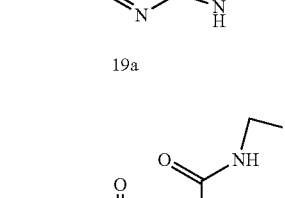 19a | 616.3 ± 20.9 | 1171 ± 128 | 818.9 ± 20.5 | 5730 ± 80 |
| 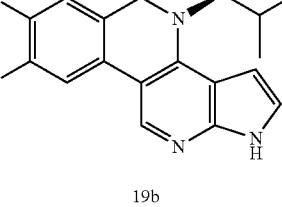 19b | 138.1 ± 4.2 | >100 | 26.58 ± 0.58 | 1163.5 ± 3.5 |
| 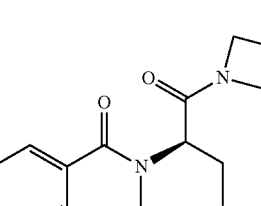 20a | 3.37 ± 0.13 | 29.6 ± 1.2 | 114.4 ± 0.6 | 73.66 ± 2.4 |
| 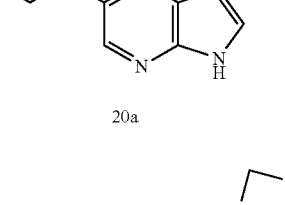 20b | 43.78 ± 3.1 | 140.2 ± 7 | 87.03 ± 0.4 | 336.3 ± 12 |

TABLE 2-continued

Enzyme assay results of the synthesized compounds.

| Compound ID: | JAK-1 IC$_{50}$ (nM) | JAK-2 IC$_{50}$ (nM) | JAK-3 IC$_{50}$ (nM) | TYK-2 IC$_{50}$ (nM) |
| --- | --- | --- | --- | --- |
| 21 | 30.17 ± 1.73 | 109.95 ± 6.1 | 75.03 ± 1.57 | 273.4 ± 2.6 |

EXAMPLES OF COMPOUND PREPARATION

Reactions were monitored by silica gel analytical thin-layer chromatography, and 254 nm UV light was used for visualization. All yields refer to isolated compounds. Unless otherwise stated, chemicals and solvents were of reagent grade and used as obtained from commercial sources without further purification. Melting points were determined using capillary tubes and are uncorrected. $^1$H Nuclear magnetic resonance spectroscopy was performed using a 300 MHz spectrometer. Infrared spectra were obtained using an FTIR spectrometer. Mass spectral analyses were performed at the Purdue University Campus-Wide Mass Spectrometry Center. HPLC analyses were performed on a Waters 1525 binary HPLC pump/Waters 2487 dual λ absorbance detector system, using a 5 μm C18 reversed phase column and UV detection at 254 nm. HPLC purities of all tested compounds were estimated from the major peak areas, which were ≥95% of the combined total peak areas.

N$^1$-(1-(Methoxymethyl)-1H-pyrrolo[2,3-b]pyridin-4-yl)-N$^3$,N$^3$-dimethylpropane-1,3-diamine (4)

Compound 3 (1 eq, 0.5 g, 2.01 mmol), N$^1$,N$^1$-dimethylpropane-1,3-diamine (0.275 g, 2.7 mol, 1.3 eq), Pd$_2$(dba)$_3$ (95 mg, 5 mol %), xantphos (120 mg, 10 mol %) and cesium carbonate (1.35 g, 4.15 mmol, 2 eq) were mixed in a 45 mL pressure tube and anhydrous dioxane (15 mL) was added to the mixture. Argon was bubbled in the reaction mixture for 2 min and then the pressure tube was capped and directly placed in a preheated oil bath at 110° C. The mixture was heated for 16 h and then allowed to cool to room temperature. CHCl$_3$ (20 mL) was added to the mixture and then it was filtered through a bed of celite and the residue was washed with additional CHCl$_3$ (20 mL). The filtrate was evaporated to give a dark residue which was purified with silica gel column chromatography using a CHCl$_3$-MeOH mixture (9:1) as the eluent to give the amine 4 as a light brown oil (0.4 g, 74%): $^1$H NMR (300 MHz, CDCl$_3$) δ 8.06 (d, J=5.5 Hz, 1H), 7.05 (t, J=13.5 Hz, 1H), 6.50 (d, J=3.6 Hz, 1H), 6.25 (s, 1H), 6.19 (d, J=5.6 Hz, 1H), 5.57 (s, 2H), 3.47 (dd, J=11.7, 5.8 Hz, 2H), 3.29 (s, 3H), 2.73 (t, J=6.3 Hz, 2H), 2.48 (s, 6H), 2.07-1.87 (m, 2H); HRESIMS m/z calcd for C$_{14}$H$_{22}$N$_4$O (MH)$^+$ 263.1866, found 263.1869.

General Procedure for the Preparation of the Amides 5a-c

A solution of the appropriate benzoyl chloride derivatives (prepared by heating the 2-bromobenzoic acid derivatives and thionyl chloride at reflux for 2 h) (1 eq, 0.9 mmol) in anhydrous DCM (5 mL) was added dropwise to an ice-cold solution of the amine 4 (0.25 g, 1 eq, 0.9 mmol) and TEA (10 eq) in anhydrous DCM (20 mL). The mixture was heated at reflux for 5 h. After cooling to room temperature the mixture was washed with saturated NaHCO$_3$ solution (1×20 mL), water (2×20 mL) and brine (1×20 mL) and dried with anhydrous sodium sulfate. The residue obtained after the evaporation of DCM was subjected to silica gel column chromatography using CHCl$_3$-MeOH as eluent to yield the desired amides 5a-c.

N-(3-(Dimethylamino)propyl)-2-bromo-N-(1-(methoxymethyl)-1H-pyrrolo[2,3-b]pyridin-4-yl)benzamide (5a)

This compound was isolated as a brown gum (0.27 g, 57%): $^1$H NMR (300 MHz, CDCl$_3$) δ 8.11 (m, 1H), 7.69 (m, 1H), 7.38 (d, J=3.6 Hz, 1H), 6.87 (m, 4H), 6.64 (m, 1H), 5.59 (s, 2H), 4.11 (m, 2H), 3.27 (s, 3H), 2.51 (m, 2H), 2.26 (s, 6H), 1.91 (m, 2H); HRESIMS m/z calcd for C$_{21}$H$_{25}$BrN$_4$O$_2$ (MH)$^+$ 445.1234/447.1216, found 445.1231/447.1215.

2-Bromo-N-(3-(dimethylamino)propyl)-4,5-dimethoxy-N-(1-(methoxymethyl)-1H-pyrrolo[2,3-b]pyridin-4-yl)benzamide (5b)

This compound was isolated as a dark brown gum (0.26 g, 54%): $^1$H NMR (300 MHz, CDCl$_3$) δ 8.16 (s, 1H), 7.38 (d, J=3.6 Hz, 1H), 6.91 (s, 1H), 6.82 (s, 1H), 6.62 (d, J=3.6 Hz, 1H), 6.47 (s, 1H), 5.59 (s, 2H), 4.07 (m, 2H), 3.75 (s, 3H), 3.40 (s, 3H), 3.26 (s, 3H), 2.60 (m, 2H), 2.31 (s, 6H), 1.93 (m, 2H); HRESIMS m/z calcd for C$_{23}$H$_{29}$BrN$_4$O$_4$ (MH)$^+$ 505.1444/507.1427, found 505.1442/507.1423.

2-Bromo-N-(3-(dimethylamino)propyl)-N-(1-(methoxymethyl)-1H-pyrrolo[2,3-b]pyridin-4-yl)-5-nitrobenzamide (5c)

This compound was isolated as a dark brown gum (0.35 g, 74%): $^1$H NMR (300 MHz, CDCl$_3$) δ 8.15 (d, J=5.0 Hz, 1H), 7.86 (s, 1H), 7.80 (dd, J=8.7, 2.6 Hz, 1H), 7.56 (d, J=8.7 Hz, 1H), 7.43 (d, J=3.6 Hz, 1H), 6.96 (d, J=5.1 Hz, 1H), 6.64 (d, J=3.7 Hz, 1H), 5.57 (s, 2H), 4.12 (s, 2H), 3.22 (s, 3H), 2.54 (s, 2H), 2.30 (s, 6H), 2.02-1.86 (m, 2H);

HRESIMS m/z calcd for $C_{21}H_{24}BrN_5O_4$ (MH)$^+$ 490.1084/492.1067, found 490.1085/492.1070.

General Procedure for the Intramolecular Direct Arylation Reaction to Afford 6a-c The benzamides 5a-c (1 eq, 0.5 mmol) were dissolved in DMA (5 mL) and Pd(OAc)$_2$ (10 mol %), Cs$_2$CO$_3$ (2 eq), Ag$_2$CO$_3$ (2 eq) and PCy$_3$·HBF$_4$ (20 mol %) were added. The reaction mixture was heated at 130° C. under Ar atmosphere for 18 h. The reaction mixture was cooled to rt and EtOAc (10 mL) was then added. The mixture was filtered through a bed of celite and the residue left on the filter pad was washed with EtOAc (about 20 mL). The filtrate was transferred to a separatory funnel and washed with water several times (5×15 mL) to remove the DMA and brine (1×15 mL). The organic layer was dried and evaporated and the residue was purified with column chromatography using CHCl$_3$-MeOH (9:1) as the eluent to give the tetracyclic compounds 6a-c.

4-(3-(Dimethylamino)propyl)-1-(methoxymethyl)-1,4-dihydro-5H-benzo[c]pyrrolo[2,3-h][1,6]naphthyridin-5-one (6a)

This compound was isolated as a brown semisolid (0.06 g, 32%): $^1$H NMR (300 MHz, CDCl$_3$) δ 9.31 (s, 1H), 8.53 (d, J=8.1 Hz, 1H), 8.39 (d, J=8.2 Hz, 1H), 7.80 (t, J=7.7 Hz, 1H), 7.57 (t, J=7.6 Hz, 1H), 7.42 (d, J=3.8 Hz, 1H), 7.02 (d, J=3.8 Hz, 1H), 5.73 (s, 2H), 4.82-4.73 (m, 2H), 3.36 (s, 3H), 2.73 (t, J=7.2 Hz, 2H), 2.42 (s, 6H), 2.23 (dd, J=15.0, 7.2 Hz, 4H); HRESIMS m/z calcd for $C_{21}H_{24}N_4O_2$ (MH)$^+$ 365.1972, found 365.1970.

4-(3-(Dimethylamino)propyl)-7,8-dimethoxy-1-(methoxymethyl)-1,4-dihydro-5H-benzo[c]pyrrolo[2,3-h][1,6]naphthyridin-5-one (6b)

This compound was isolated as a light brown oil (0.06 g, 28%): $^1$H NMR (300 MHz, CDCl$_3$) δ 9.19 (s, 1H), 7.89 (s, 1H), 7.71 (s, 1H), 7.41 (d, J=3.8 Hz, 1H), 6.99 (d, J=3.8 Hz, 1H), 5.73 (s, 2H), 4.78 (s, 2H), 4.10 (s, 3H), 4.04 (s, 3H), 3.35 (m, 2H), 2.78 (m, 2H), 2.45 (s, 6H), 2.27 (m, 2H); HRESIMS m/z calcd for $C_{23}H_{28}BrN_4O_4$ (MH)$^+$ 425.2183, found 425.2187.

4-(3-(Dimethylamino)propyl)-11-(methoxymethyl)-7-nitro-4,11-dihydro-5H-1,4,11-triazadibenzo[cd,h]azulen-5-one (6c)

This compound was isolated as a yellow solid (0.03 g, 14%): mp 125-127° C. $^1$H NMR (300 MHz, CDCl$_3$) δ 9.17 (d, J=2.5 Hz, 1H), 8.24 (d, J=5.6 Hz, 1H), 8.19 (dd, J=8.8, 2.5 Hz, 1H), 7.76 (s, 1H), 7.71 (d, J=8.8 Hz, 1H), 6.80 (d, J=5.8 Hz, 1H), 5.66 (s, 2H), 4.18 (m, 2H), 3.37 (s, 3H), 2.61 (s, 2H), 2.41 (s, 6H), 2.08 (m, 2H); HRESIMS m/z calcd for $C_{21}H_{23}BrN_5O_4$ (MH)$^+$ 410.1823, found 410.1820.

4-(3-(Dimethylamino)propyl)-7,8-dimethoxy-1,4-dihydro-5H-benzo[c]pyrrolo[2,3-h][1,6]naphthyridin-5-one (1)

Compound 6b (0.05 g, 0.13 mmol) was dissolved in THF (10 mL) and concd HCl (2 mL) was added to the solution. The mixture was heated at 80° C. for 18 h and then cooled to room temperature. The THF was evaporated under reduced pressure and the residue left was treated with saturated NaHCO$_3$ solution until the effervescence ceased. The mixture was extracted with CHCl$_3$ (3×15 mL) and the combined organic layer was washed with water (2×10 ml) and brine (1×15 ml), dried with sodium sulfate and evaporated to give a light brown residue. The residue was purified using column chromatography CHCl$_3$-MeOH (8.5:1.5) to give the final compound 1 as a light brown foam (26 mg, 59%): mp 152-153° C. $^1$H NMR (300 MHz, DMSO-d$_6$) δ 12.16 (s, 1H), 9.38 (s, 1H), 8.68 (d, J=8.1 Hz, 1H), 8.36 (d, J=8.0 Hz, 1H), 7.85 (t, J=7.6 Hz, 1H), 7.66-7.47 (m, 2H), 6.94 (m, 1H), 4.74-4.59 (m, 2H), 2.66 (s, 2H), 2.33 (s, 6H), 2.03 (m, 3H); MALDIMS m/z (rel intensity) 381 (MH)$^+$; HRESIMS calcd for $C_{21}H_{25}N_4O_3$ (MH)$^+$ 381.1927, found 381.1920; C18 HPLC purity, 100% (MeOH—H$_2$O, 85:15).

4-(3-(Dimethylamino)propyl)-7,8-dimethoxy-1,4-dihydro-5H-benzo[c]pyrrolo[2,3-h][1,6]naphthyridin-5-one (7a)

Following the same procedures as for 1, this compound was prepared from 6a and isolated as a dark brown solid (0.026 g, 58%): mp 185-187° C. IR (thin film) 2950, 1648, 1578, 1418, 1338, 1314, 1036 cm$^{-1}$; $^1$H NMR (300 MHz, DMSO-d$_6$) δ 12.11 (s, 1H), 9.40 (s, 1H), 8.04 (s, 1H), 7.73 (s, 1H), 7.55 (s, 1H), 6.93 (s, 1H), 4.66 (m, 2H), 4.05 (s, 3H), 3.91 (s, 3H), 2.63-2.48 (m, 2H), 2.26 (s, 6H), 1.99 (m, 2H); MALDIMS m/z (rel intensity) 321 (MH)$^+$; HRESIMS calcd for $C_{19}H_{21}N_4O$ (MH)$^+$ 321.1716, found 321.1709; C18 HPLC purity, 99.65% (MeOH—H$_2$O, 85:15).

4-(3-(Dimethylamino)propyl)-7-nitro-1,4-dihydro-5H-benzo[c]pyrrolo[2,3-h][1,6]naphthyridin-5-one (7b)

Following the same procedures as for 1, this compound was prepared from 6c and isolated as a yellow powder (0.032 g, 71%): mp 205-207° C. IR (thin film) 2864, 1667, 1611, 1572, 1519, 1491, 1433, 1403, 1328, 1135, 1077 cm$^{-1}$; $^1$H NMR (300 MHz, DMSO-d$_6$) δ 12.35 (s, 1H), 9.44 (s, 1H), 9.04 (d, J=2.6 Hz, 1H), 8.93 (d, J=9.2 Hz, 1H), 8.54 (dd, J=9.0, 2.6 Hz, 1H), 7.64 (s, 1H), 7.01 (s, 1H), 4.66 (m, 2H), 2.52 (t, J=1.3 Hz, 2H), 2.24 (s, 6H), 1.99 (m, 3H); MALDIMS m/z (rel intensity) 366 (MH)$^+$; HRESIMS calcd for $C_{19}H_{20}N_5O_3$ (MH)$^+$ 366.1566, found 366.1560; C18 HPLC purity, 100% (MeOH—H$_2$O, 85:15).

1-((2-(Trimethylsilyl)ethoxy)methyl)-1H-pyrrolo[2,3-b]pyridin-4-amine (9)

SEM-protected 4-bromo-7-azaindole 8 (2 g, 8.3 mmol) was added to a mixture of xantphos (0.48 g, 0.83 mmol), Pd(OAc)$_2$ (0.093 g, 0.41 mmol), benzophenone imine (1.8 g, 9.93 mmol) and Cs$_2$CO$_3$ (5.4 g, 16.59 mmol) in anhydrous dioxane (50 mL). The reaction mixture was added to a 150 mL pressure vessel, degassed with Ar for 5 min and heated at 110° C. for 18 h. The reaction mixture was cooled to room temperature mixed with chloroform (50 mL) and filtered through a bed of celite. The filterate was evaporated and the residue was dissolved in MeOH (100 mL). Sodium acetate (1.5 g, 19 mmol) and hydroxylamine hydrochloride (0.95 g, 13.7 mmol) were added to the solution and the mixture was stirred at room temperature for 10 h. MeOH was evaporated and the residue was partitioned between NaOH solution (1 N, 100 mL) and methylene chloride (100 mL). The organic layer was washed with water (2×50 mL) and brine (1×20 mL) and dried. Column chromatography of the residue obtained after evaporation of the solvent (SiO$_2$/CHCl$_3$:

MeOH-9:1) gave 9 as a yellow solid (1.3 g, 81%): mp 135-137° C. $^1$H NMR (300 MHz, CDCl$_3$) δ 8.04 (d, J=5.4 Hz, 1H), 7.17 (d, J=3.7 Hz, 1H), 6.42 (d, J=3.7 Hz, 1H), 6.35 (d, J=5.4 Hz, 1H), 5.64 (s, 2H), 4.42 (s, 2H), 3.59-3.45 (m, 2H), 0.98-0.85 (m, 2H), −0.04-−0.11 (m, 9H).

2-Iodo-4,5-dimethoxy-N-(1-((2-(trimethylsilyl)ethoxy)methyl)-1H-pyrrolo[2,3-b]pyridin-4-yl)benzamide (10)

A solution of 2-iodo-4,5-dimethoxybenzoyl chloride (prepared by heating a mixture of the acid and thionyl chloride at reflux for 2 h) (0.342 g, 0.3 mmol) in anhydrous DCM (5 mL) was added dropwise to an ice-cold solution of the amine 9 (0.4 g, 0.3 mmol) and TEA (10 eq) in anhydrous DCM (20 mL). The mixture was heated at reflux for 5 h. After cooling to room temperature, the mixture was washed with saturated NaHCO$_3$ solution (1×20 mL), water (2×20 mL) and brine (1×20 mL) and dried with anhydrous sodium sulfate. The residue obtained after the evaporation of DCM was subjected to column chromatography using CHCl$_3$-EtOAc (8:2) as eluent to yield the desired amides 10 as a creamy white solid (0.43 g, 58%): mp 165-167° C. $^1$H NMR (300 MHz, CDCl$_3$) δ 8.37 (d, J=5.6 Hz, 1H), 8.20-8.02 (m, 2H), 7.36 (d, J=3.8 Hz, 1H), 7.32 (s, 1H), 6.66 (s, 1H), 5.75 (s, 2H), 3.95 (s, 3H), 3.93 (s, 3H), 3.59 (m, 2H), 1.04-0.78 (m, 2H), −0.05 (s, 9H); HRESIMS m/z calcd for C$_{22}$H$_{28}$IN$_3$O$_4$Si (MH)$^+$ 554.0967, found 554.0968.

General Procedures for Compounds 11a-c

A suspension of sodium hydride (0.72 mmol) in anhydrous DMF (5 mL) was cooled in an ice bath. A solution of 10 (0.2 g, 0.36 mmol) in DMF (2 mL) was added dropwise to the sodium hydride suspension over 5 min. The mixture was stirred at rt for 1 h and then the alkylbromide (0.72 mmol) was added all at once. The reaction mixture was stirred at room temperature for 18 h and then quenched with ice-cold water (25 mL). The mixture was extracted with EtOAc (3×15 mL) and the combined organic layers were washed with water (2×15 mL) and brine (1×20 mL) and dried. Purification of the residue obtained after evaporating the EtOAc layer yielded 15a-c.

tert-Butyl N-(2-iodo-4,5-dimethoxybenzoyl)-N-(1-((2-(trimethylsilyl)ethoxy)methyl)-1H-pyrrolo[2,3-b]pyridin-4-yl)glycinate (11a)

Compound 15a was obtained as a creamy white solid (0.22 g, 91%): mp 113-115° C. $^1$H NMR (300 MHz, CDCl$_3$) δ 8.17 (s, 1H), 7.42 (d, J=3.6 Hz, 1H), 7.11 (s, 1H), 7.05-6.99 (m, 1H), 6.78 (s, 1H), 6.67 (s, 1H), 5.76 (s, 2H), 4.54 (s, 1H), 3.80 (s, 2H), 3.61-3.52 (m, 2H), 3.47 (s, 2H), 1.50 (s, 9H), 0.96-0.87 (m, 2H), −0.06 (s, 9H); HRESIMS m/z calcd for C$_{28}$H$_{38}$IN$_3$O$_6$Si (MH)$^+$ 668.1647, found 668.1644.

Methyl N-(2-Iodo-4,5-dimethoxybenzoyl)-N-(1-((2-(trimethylsilyl)ethoxy)methyl)-1H-pyrrolo[2,3-b]pyridin-4-yl)glycinate (11b)

This compound was isolated as a yellow oil (0.2 g, 88%). $^1$H NMR (300 MHz, CDCl$_3$) δ 8.17 (d, J=5.4 Hz, 1H), 7.41 (d, J=3.6 Hz, 1H), 7.09 (s, 1H), 7.04 (d, J=5.4 Hz, 1H), 6.74 (d, J=3.6 Hz, 1H), 6.62 (s, 1H), 5.70 (s, 2H), 4.67 (s, 2H), 3.80 (s, 3H), 3.78 (s, 3H), 3.58-3.47 (m, 2H), 3.44 (s, 3H), 0.97-0.82 (m, 2H), −0.05-−0.10 (s, 9H); HRESIMS m/z calcd for C$_{25}$H$_{32}$IN$_3$O$_4$Si (MH)$^+$ 626.1177, found 626.1176.

Ethyl 2-(2-Iodo-4,5-dimethoxy-N-(1-((2-(trimethylsilyl)ethoxy)methyl)-1H-pyrrolo[2,3-b]pyridin-4-yl)benzamido)butanoate (11c)

This compound was isolated as a yellow oil (0.2 g, 83%). $^1$H NMR (300 MHz, CDCl$_3$) δ 8.16 (d, J=5.0 Hz, 1H), 7.38 (d, J=3.7 Hz, 1H), 7.06 (m, 2H), 6.92 (m, 1H), 6.53 (s, 1H), 5.66 (s, 2H), 4.67-4.56 (m, 1H), 4.32 (d, J=7.3 Hz, 3H), 3.75 (s, 3H), 3.51-3.45 (m, 2H), 3.36 (s, 3H), 1.58 (s, 5H), 1.36 (t, J=7.1 Hz, 3H), 1.01 (t, J=7.3 Hz, 3H), 0.93-0.84 (m, 3H), −0.07-−0.11 (s, 9H); HRESIMS m/z calcd for C$_{28}$H$_{38}$IN$_3$O$_6$Si (MH)$^+$ 668.1647, found 668.1651.

tert-Butyl 2-(7,8-Dimethoxy-5-oxo-1-((2-(trimethylsilyl)ethoxy)methyl)-1,5-dihydro-4H-benzo[c]pyrrolo[2,3-h][1,6]naphthyridin-4-yl)acetate (12a)

Pd(OAc)$_2$ (9 mg, 0.037 mmol), K$_2$CO$_3$ (0.15 g, 1.12 mmol), Ag$_2$CO$_3$ (0.2 g, 0.74 mmol) and PCy$_3$.HBF$_4$ (28 mg, 0.075 mmol) were added to a solution of benzamide 11a (0.25 g, 0.37 mmol) in DMA (5 mL). The reaction mixture was heated at 130° C. under Ar atmosphere for 18 h. The reaction mixture was cooled to rt and EtOAc (10 mL) was then added. The mixture was filtered through a bed of celite and the residue left was washed thoroughly with EtOAc (about 20 mL). The filtrate was transferred to a separatory funnel and washed with water several times to remove the DMA (5×15 mL) and brine (1×15 mL). The organic layer was dried and evaporated and the residue was purified with silica gel column chromatography using CHCl$_3$-MeOH (9:1) as the eluent to give the tetracyclic compound 12a (0.15 g, 74%) as a yellow solid: mp 156-158° C. $^1$H NMR (300 MHz, CDCl$_3$) δ 9.18 (s, 1H), 7.93 (s, 1H), 7.71 (s, 1H), 7.40 (d, J=3.9 Hz, 1H), 6.81 (d, J=3.5 Hz, 1H), 5.79 (s, 2H), 5.45 (s, 2H), 4.12 (s, 3H), 4.04 (s, 3H), 3.65-3.47 (m, 3H), 1.53-1.41 (m, 9H), 1.03-0.78 (m, 2H), −0.00-−0.11 (m, 9H); HRESIMS m/z calcd for C$_{28}$H$_{27}$N$_3$O$_6$Si (MH)$^+$ 540.2524, found 540.2522.

Methyl 2-(7,8-Dimethoxy-5-oxo-1-((2-(trimethylsilyl)ethoxy)methyl)-1,5-dihydro-4H-benzo[c]pyrrolo[2,3-h][1,6]naphthyridin-4-yl)acetate (12b)

Using the same procedure used for 12a, compound 12b was prepared from 11b and was isolated as a yellow solid (0.1 g, 62%): mp 136-138° C. $^1$H NMR (300 MHz, CDCl$_3$) δ 9.18 (s, 1H), 7.91 (s, 1H), 7.70 (s, 1H), 7.40 (d, J=3.7 Hz, 1H), 6.76 (d, J=3.8 Hz, 1H), 5.81 (s, 2H), 5.56 (s, 2H), 4.12 (s, 3H), 4.04 (s, 3H), 3.80 (s, 4H), 3.69-3.54 (m, 2H), 1.00-0.84 (m, 2H), −0.02-−0.07 (s, 9H); HRESIMS m/z calcd for C$_{25}$H$_{31}$N$_3$O$_6$Si (MH)$^+$ 498.2055, found 498.2047.

Ethyl 2-(7,8-Dimethoxy-5-oxo-1-((2-(trimethylsilyl)ethoxy)methyl)-1,5-dihydro-4H-benzo[c]pyrrolo[2,3-h][1,6]naphthyridin-4-yl)butanoate (12c)

This compound was prepared from 11c and isolated as a yellow solid (0.09 g, 44%): mp 152-154° C. $^1$H NMR (300 MHz, CDCl$_3$) δ 9.19 (s, 1H), 7.85 (s, 1H), 7.70 (s, 1H), 7.42 (d, J=3.6 Hz, 1H), 6.83 (s, 1H), 5.78 (s, 2H), 4.11 (s, 3H), 4.01 (s, 3H), 3.67-3.54 (m, 3H), 3.48 (q, J=7.0 Hz, 3H), 2.51 (m, 2H), 0.9 (m, 2H), −0.04 (s, 9H); HRESIMS m/z calcd for C$_{28}$H$_{37}$IN$_3$O$_6$Si (MH)$^+$ 540.2524, found 540.2523.

tert-Butyl 2-(7,8-Dimethoxy-5-oxo-1,5-dihydro-4H-benzo[c]pyrrolo[2,3-h][1,6]naphthyridin-4-yl)acetate (13a)

Compound 12a (0.1 g, 0.18 mmol) was dissolved in methylene chloride (5 mL) and TFA (5 mL) was added to the solution dropwise. The mixture was stirred at room temperature for 2 h and then the solvent was evaporated. The residue obtained was dissolved in MeOH (5 mL) and NaOH solution (2N, 2 mL). Ethylenediamine (1 mL) was added and the mixture was stirred overnight at room temperature. The mixture was acidified with TFA and extracted with $CHCl_3$ (3×10 mL). The combined organic layer was washed with water and brine (15 mL each), dried and evaporated to yield 13a as a white solid (20 mg, 26%): mp 212-214° C. IR (thin film) 2926, 1744, 1647, 1612, 1583, 1462, 1427, 1389, 1327, 1225, 1244, 1210, 1156, 1107, 1029 $cm^{-1}$; $^1H$ NMR (300 MHz, DMSO) δ 12.19-12.08 (s, 1H), 9.42 (s, 1H), 8.32 (s, 1H), 8.12-8.04 (m, 1H), 7.72 (s, 1H), 7.58-7.46 (m, 1H), 6.67-6.58 (m, 1H), 5.38 (s, 2H), 4.06 (s, 3H), 3.91 (s, 3H), 1.44 (s, 9H); MALDIMS m/z (rel intensity) 410 $(MH)^+$; HRESIMS calcd for $C_{22}H_{23}N_3O_5$ $(MH)^+$ 410.1711, found 410.1709; C18 HPLC purity, 96.64% ($MeOH-H_2O$, 85:15).

Methyl 2-(7,8-Dimethoxy-5-oxo-1,5-dihydro-4H-benzo[c]pyrrolo[2,3-h][1,6]naphthyridin-4-yl)acetate (13b)

This compound was prepared form 12b using the procedure described for 13a and was isolated as a white solid (25 mg, 45%): mp 212-214° C. IR (thin film) 2964, 1752, 1658, 1612, 1575, 1513, 1458, 1427, 1387, 1351, 1370, 1302, 1267, 1242, 1177, 1167, 1143, 1105, 1077, 1003 $cm^{-1}$; $^1H$ NMR (300 MHz, DMSO) δ 12.16 (s, 1H), 9.41 (s, 1H), 8.06 (s, 1H), 7.70 (s, 1H), 7.51 (s, 1H), 6.59 (s, 1H), 5.48 (s, 2H), 4.05 (s, 3H), 3.90 (d, J=3.8 Hz, 3H), 3.71 (d, J=5.8 Hz, 3H); MALDIMS m/z (rel intensity) 368 $(MH)^+$; HRESIMS calcd for $C_{19}H_{17}N_3O_5$ $(MH)^+$ 368.1241, found 368.1243; C18 HPLC purity, 98% ($MeOH-H_2O$, 85:15).

Ethyl 2-(7,8-Dimethoxy-5-oxo-1,5-dihydro-4H-benzo[c]pyrrolo[2,3-h][1,6]naphthyridin-4-yl)butanoate (13c)

This compound was prepared form compound 12c using the procedure described for 13a and was isolated as a white solid (37 mg, 60%): mp 235-237° C. IR (thin film) 2979, 1725, 1640, 1610, 1572, 1514, 1460, 1420, 1386, 1368, 1339, 1318, 1269, 1244, 1211, 1141, 1110, 1090, 1033, 1014 $cm^{-1}$; $^1H$ NMR (300 MHz, DMSO) δ 12.18 (s, 1H), 9.41 (s, 1H), 8.04 (s, 1H), 7.64 (s, 1H), 7.53 (s, 1H), 6.95 (s, 1H), 5.73 (d, J=7.6 Hz, 1H), 4.06 (d, J=4.7 Hz, 1H), 4.04 (s, 3H), 3.88 (s, 3H), 2.33 (dd, J=40.8, 7.6 Hz, 2H), 1.05 (t, J=7.1 Hz, 3H), 0.79 (t, J=7.5 Hz, 3H); MALDIMS m/z (rel intensity) 410 $(MH)^+$; HRESIMS calcd for $C_{22}H_{23}N_3O_5$ $(MH)^+$ 410.1711, found 410.1711; C18 HPLC purity, 100% ($MeOH-H_2O$, 85:15).

Preparation of the Amides 14a-l

2-Bromo-3,4-dimethoxybenzoic acid (0.3 g, 1.14 mmol) was added to thionyl chloride (4 mL) and catalytic amount of DMF. The reaction mixture was heated at reflux for 3 h and then the thionyl chloride was evaporated to afford the corresponding acid chloride. The appropriate amine (1.2 mmol) was dissolved in DCM (5 mL) in an ice bath and mixed with TEA (5 mmol) in a vial, and the acid chloride was dissolved in DCM (2 mL) and added drop wise to the amine solution. The reaction mixture was stirred overnight at room temperature and then the reaction was quenched with a saturated solution of sodium carbonate. The organic layer was then separated, washed with water, dried and evaporated to give a residue. The residue was purified with column chromatography using either $CHCl_3$/MeOH or EtOAc/hexanes mixtures to give the amides 14a-l as white solids.

2-Bromo-N-cyclohexyl-4,5-dimethoxybenzamide (14a)

This compound was isolated as a white solid (0.35 g, 89%): mp 185-187° C. $^1H$ NMR (300 MHz, $CDCl_3$) δ 7.21 (s, 1H), 6.98 (s, 1H), 6.13 (s, 1H), 3.99 (s, 1H), 3.89 (s, 6H), 2.04 (d, J=12.6 Hz, 2H), 1.75 (d, J=13.1 Hz, 2H), 1.50-1.17 (m, 6H); HRESIMS m/z calcd for $C_{15}H_{20}BrNO_3$ $(MH)^+$ 342.0699/344.0681, found 342.0701/344.0683.

2-Bromo-N-(cyclohexylmethyl)-4,5-dimethoxybenzamide (14b)

This compound was isolated as a white solid (0.38 g, 93%): mp 163-165° C. $^1H$ NMR (300 MHz, $CDCl_3$) δ 7.25 (s, 1H), 6.99 (s, 1H), 6.33 (s, 1H), 3.90 (d, J=0.8 Hz, 6H), 3.31 (t, J=6.3 Hz, 2H), 1.89-1.65 (m, 6H), 1.23 (dd, J=25.3, 15.9 Hz, 4H), 1.13-0.94 (m, 2H); HRESIMS m/z calcd for $C_{16}H_{22}BrNO_3$ $(MH)^+$ 356.0856/358.0837, found 356.0855/358.0833.

2-Bromo-N-cycloheptyl-4,5-dimethoxybenzamide (14c)

This compound was isolated as a white solid (0.36 g, 88%): mp 157-158° C. $^1H$ NMR (300 MHz, $CDCl_3$) δ 7.20 (s, 1H), 6.99 (d, J=5.6 Hz, 1H), 6.20 (d, J=7.8 Hz, 1H), 4.15 (d, J=12.1 Hz, 1H), 3.89 (s, 6H), 2.06 (dd, J=16.2, 6.0 Hz, 2H), 1.76-1.50 (m, 13H); HRESIMS m/z calcd for $C_{16}H_{22}BrNO_3$ $(MH)^+$ 356.0856/358.0837, found 356.0855/358.0837.

2-Bromo-N-cyclooctyl-4,5-dimethoxybenzamide (14d)

This compound was isolated as a white solid (0.32 g, 75%): mp 145-147° C. $^1H$ NMR (300 MHz, $CDCl_3$) δ 7.21 (s, 1H), 6.99 (d, J=5.6 Hz, 1H), 6.23 (d, J=8.0 Hz, 1H), 4.27-4.14 (m, 1H), 3.89 (s, 6H), 2.03-1.90 (m, 2H), 1.64 (m, 15H); HRESIMS m/z calcd for $C_{17}H_{24}BrNO_3$ $(MH)^+$ 370.1012/372.0994, found 370.1012/372.0997.

2-Bromo-4,5-dimethoxy-N-(1-methylpiperidin-4-yl) benzamide (14e)

This compound was isolated as a white solid (0.35 g, 85%): mp 201-204° C. $^1H$ NMR (300 MHz, $CDCl_3$) δ 7.19 (s, 1H), 6.99 (s, 1H), 6.17 (s, 1H), 4.04 (s, 1H), 3.89 (s, 6H), 2.85 (d, J=11.6 Hz, 2H), 2.33 (s, 3H), 2.22 (t, J=11.2 Hz, 2H), 2.09 (d, J=11.1 Hz, 2H), 1.67 (dd, J=22.1, 12.5 Hz, 2H); HRESIMS m/z calcd for $C_{15}H_{21}BrN_2O_3$ $(MH)^+$ 357.0808/359.0789, found 357.0809/359.0791.

tert-butyl 4-(2-Bromo-4,5-dimethoxybenzamido) piperidine-1-carboxylate (14f)

This compound was isolated as a white solid (0.4 g, 79%): mp 210-215° C. $^1H$ NMR (300 MHz, $CDCl_3$) δ 7.19 (s, 1H), 6.97 (s, 1H), 6.20 (d, J=7.9 Hz, 1H), 4.18-3.98 (m, 3H), 3.89 (s, 6H), 2.97 (t, J=11.5 Hz, 2H), 2.03 (dd, J=12.7, 3.5 Hz, 2H), 1.46 (s, 9H); HRESIMS m/z calcd for $C_{19}H_{27}BrN_2O_3$ (M+Na)$^+$ 465.0995/467.0977, found 465.0995/467.0977.

tert-butyl (R)-3-(2-bromo-4,5-dimethoxybenzamido) pyrrolidine-1-carboxylate (14g)

This compound was isolated as a white solid (0.38 g, 77%): mp 241-243° C. $^1$H NMR (300 MHz, CDCl$_3$) δ 7.23 (s, 1H), 6.99 (s, 1H), 6.39 (s, 1H), 4.66 (s, 1H), 3.90 (s, 6H), 3.68 (dd, J=11.5, 5.9 Hz, 1H), 3.50 (sm 2H), 3.41 (m, 1H), 2.23 (dt, J=13.7, 6.8 Hz, 1H), 2.02 (m, 1H), 1.47 (s, 9H); HRESIMS m/z calcd for $C_{18}H_{25}BrN_2O_5$ (M+Na)$^+$ 451.0839/453.0821, found 451.0836/453.0819.

tert-butyl (R)-3-(2-bromo-4,5-dimethoxybenzamido) piperidine-1-carboxylate (14h)

This compound was isolated as a white solid (0.41 g, 80%): mp 235-236° C. $^1$H NMR (300 MHz, CDCl$_3$) δ 7.27 (s, 1H), 6.99 (s, 1H), 6.51 (d, J=7.3 Hz, 1H), 4.19 (s, 1H), 3.90 (s, 6H), 3.63-3.51 (m, 3H), 3.35-3.20 (m, 1H), 1.93-1.71 (m, 3H), 1.44 (s, 9H); HRESIMS m/z calcd for $C_{19}H_{27}BrN_2O_5$ (M+Na)$^+$ 465.0995/467.0977, found 465.0991/467.0979.

Methyl (2-bromo-4,5-dimethoxybenzoyl)-D-valinate (14i)

This compound was isolated as a white solid (0.38 g, 88%): mp 178-180° C. $^1$H NMR (300 MHz, CDCl$_3$) δ 7.02 (s, 1H), 6.86 (d, J=8.4 Hz, 1H), 4.78 (dd, J=8.6, 4.7 Hz, 1H), 3.90 (d, J=4.7 Hz, 6H), 3.78 (s, 3H), 2.32 (qd, J=11.6, 6.9 Hz, 1H), 1.06 (d, J=6.9 Hz, 3H), 1.02 (d, J=6.9 Hz, 3H); HRESIMS m/z calcd for $C_{15}H_{20}BrNO_5$ (M+Na)$^+$ 396.0417/398.0398, found 396.0412/398.0392.

Methyl (2-bromo-4,5-dimethoxybenzoyl)-L-valinate (14j)

This compound was isolated as a white solid (0.37 g, 87%): mp 181-183° C. $^1$H NMR (300 MHz, CDCl$_3$) δ 7.02 (s, 1H), 6.86 (d, J=8.6 Hz, 1H), 4.78 (dd, J=8.6, 4.7 Hz, 1H), 3.90 (d, J=4.7 Hz, 6H), 3.78 (s, 3H), 2.38-2.24 (m, 1H), 1.06 (d, J=6.9 Hz, 3H), 1.02 (d, J=6.9 Hz, 3H); HRESIMS m/z calcd for $C_{15}H_{20}BrNO_5$ (M+Na)$^+$ 396.0417/398.0398, found 396.0421/398.0403.

Methyl (R)-2-(2-bromo-4,5-dimethoxybenzamido) butanoate (14k)

This compound was isolated as a white solid (0.34 g, 82%): mp 165-168° C. $^1$H NMR (300 MHz, CDCl$_3$) δ 7.26 (s, 1H), 7.02 (s, 1H), 6.91 (d, J=7.8 Hz, 1H), 4.79 (dd, J=13.0, 6.5 Hz, 1H), 3.91 (s, 3H), 3.89 (s, 3H), 3.80 (s, 3H), 2.13-1.97 (m, 1H), 1.88 (td, J=14.1, 7.1 Hz, 1H), 1.02 (t, J=7.5 Hz, 3H); HRESIMS m/z calcd for $C_{14}H_{18}BrNO_5$ (M+Na)$^+$ 382.0260/384.0241, found 382.0263/384.0246.

Methyl (S)-2-(2-bromo-4,5-dimethoxybenzamido) butanoate (14l)

This compound was isolated as a white solid (0.37 g, 89%): mp 185-187° C. $^1$H NMR (300 MHz, CDCl$_3$) δ 7.25 (s, 1H), 7.01 (s, 1H), 6.92 (d, J=7.1 Hz, 1H), 4.79 (td, J=6.5, 5.4 Hz, 1H), 3.90 (d, J=3.8 Hz, 6H), 3.79 (s, 3H), 2.12-1.97 (m, 1H), 1.88 (td, J=14.1, 7.1 Hz, 1H), 1.01 (t, J=7.5 Hz, 3H; HRESIMS m/z calcd for $C_{14}H_{18}BrNO_5$ (M+Na)$^+$ 360.0441/3620.0422, found 382.0258/384.0237.

General Procedure for the Synthesis of Compounds 16a-l

A screw-capped vial with a Teflon cap was charged with SEM-protected 4-iodo-7-azaindole (15) (0.26 mmol, 1 eq), amides 14a-l (0.26 mmol, 1.05 eq), Pd(OTFA)$_2$ (10 mol %), TFP (20 mol %), norborene (0.26 mmol, 1.05 eq) and cesium carbonate (3 eq). The atmosphere of the vial was evacuated and refilled with argon once and then the solvent (4 mL) was added via syringe and the vial was evacuated and refilled with argon twice. The reaction mixture was heated at the stated temperatures and time in Table 1 and was then cooled to room temperature. The reaction mixture was filtered through a pad of celite and solvent was evaporated and the residue obtained was loaded on a silica gel column and the mixture was purified using EtOAc/hex mixture to give compounds 16a-l.

4-Cyclohexyl-7,8-dimethoxy-1-((2-(trimethylsilyl) ethoxy)methyl)-1,4-dihydro-5H-benzo[c]pyrrolo[2,3-h][1,6]naphthyridin-5-one (16a)

Compound 16a was isolated as a yellowish powder (0.1 g, 78%): mp 198-200° C. $^1$H NMR (500 MHz, CDCl$_3$) δ 9.18 (s, 1H), 7.93 (s, 1H), 7.69 (d, J=28.6 Hz, 1H), 7.45 (d, J=3.7 Hz, 1H), 6.83 (d, J=3.8 Hz, 1H), 5.82 (s, 2H), 4.97 (t, J=11.8 Hz, 1H), 4.16 (s, 3H), 4.09 (s, 3H), 3.72-3.59 (m, 2H), 3.08-2.91 (m, 2H), 2.05 (t, J=14.5 Hz, 4H), 1.86 (s, 1H), 1.52 (dd, J=23.9, 16.1 Hz, 3H), 1.05-0.95 (m, 2H), 0.05--0.02 (s, 9H); HRESIMS m/z calcd for $C_{28}H_{37}N_3O_4Si$ (MH)$^+$ 508.2626, found 508.2629.

4-(Cyclohexylmethyl)-7,8-dimethoxy-1-((2-(trimethylsilyl)ethoxy)methyl)-1,4-dihydro-5H-benzo[c]pyrrolo[2,3-h][1,6]naphthyridin-5-one (16b)

This compound was isolated as a yellow solid (0.11 g, 81%): mp 122-123° C. $^1$H NMR (300 MHz, CDCl$_3$) δ 9.18 (s, 1H), 7.93 (s, 1H), 7.70 (s, 1H), 7.42 (d, J=3.7 Hz, 1H), 6.85 (d, J=3.8 Hz, 1H), 5.80 (s, 2H), 4.11 (s, 3H), 4.05 (s, 3H), 3.68-3.52 (m, 2H), 1.65 (m, 9H), 1.22 (m, 3H), 1.01-0.85 (m, 2H), −0.01--0.08 (s, 9H); HRESIMS m/z calcd for $C_{29}H_{39}N_3O_4Si$ (MH)$^+$ 522.2782, found 522.2780.

4-Cycloheptyl-7,8-dimethoxy-1-((2-(trimethylsilyl) ethoxy)methyl)-1,4-dihydro-5H-benzo[c]pyrrolo[2,3-h][1,6]naphthyridin-5-one (16c)

This compound was isolated as a yellowish-white solid (70 mg, 50%): mp 184-186° C. $^1$H NMR (500 MHz, CDCl$_3$) δ 9.20 (s, 1H), 7.94 (s, 1H), 7.73 (s, 1H), 7.46 (d, J=3.7 Hz, 1H), 6.94 (d, J=3.7 Hz, 1H), 5.81 (d, J=8.7 Hz, 2H), 5.24 (d, J=10.4 Hz, 1H), 4.16 (s, 3H), 4.09 (s, 3H), 3.71-3.55 (m, 3H), 2.99-2.85 (m, 2H), 2.18-2.08 (m, 2H), 2.01 (s, 2H), 1.80 (d, J=4.3 Hz, 4H), 1.67 (d, J=19.6 Hz, 7H), 1.06-0.96 (m, 3H), 0.06--0.00 (m, 9H); HRESIMS m/z calcd for $C_{29}H_{39}N_3O_4Si$ (MH)$^+$ 522.2782, found 522.2782.

4-Cyclooctyl-7,8-dimethoxy-1-((2-(trimethylsilyl) ethoxy)methyl)-1,4-dihydro-5H-benzo[c]pyrrolo[2,3-h][1,6]naphthyridin-5-one (16d)

This compound was isolated as a creamy white powder (84 mg, 58%): mp 166-168° C. $^1$H NMR (500 MHz, CDCl$_3$)

δ 9.20 (s, 1H), 7.93 (s, 1H), 7.72 (d, J=10.5 Hz, 1H), 7.47 (d, J=3.7 Hz, 1H), 6.96 (d, J=3.8 Hz, 1H), 5.81 (d, J=9.8 Hz, 2H), 5.25 (t, J=9.7 Hz, 1H), 4.16 (s, 3H), 4.09 (s, 3H), 3.71-3.59 (m, 2H), 3.00-2.89 (m, 2H), 2.10 (dt, J=28.9, 14.4 Hz, 2H), 2.05-1.96 (m, 3H), 1.89-1.78 (m, 2H), 1.74-1.63 (m, 7H), 1.01 (dd, J=10.8, 5.6 Hz, 2H), 0.04--0.00 (s, 9H); HRESIMS m/z calcd for $C_{30}H_{41}N_3O_4Si$ (MH)$^+$ 536.2939, found 536.2939.

7,8-Dimethoxy-4-(1-methylpiperidin-4-yl)-1-((2-(trimethylsilyl)ethoxy)methyl)-1,4-dihydro-5H-benzo[c]pyrrolo[2,3-h][1,6]naphthyridin-5-one (16e)

This compound was isolated as a yellow oil (85 mg, 60%): $^1$H NMR (500 MHz, CDCl$_3$) δ 9.18 (s, 1H), 7.92 (s, 1H), 7.72 (s, 1H), 7.47 (d, J=3.5 Hz, 1H), 6.80 (s, 1H), 5.82 (s, 2H), 5.02 (s, 1H), 4.16 (s, 3H), 4.10 (s, 3H), 3.69-3.61 (m, 2H), 3.42 (d, J=12.0 Hz, 2H), 3.24 (s, 2H), 2.53 (s, 2H), 1.98 (d, J=10.8 Hz, 2H), 1.06-0.94 (m, 2H), 0.02 (s, 9H); HRESIMS m/z calcd for $C_{28}H_{38}N_4O_4Si$ (MH)$^+$ 523.2735, found 523.2737.

tert-Butyl 4-(7,8-Dimethoxy-5-oxo-1-((2-(trimethylsilyl)ethoxy)methyl)-1,5-dihydro-4H-benzo[c]pyrrolo[2,3-h][1,6]naphthyridin-4-yl)piperidine 1-Carboxylate (16f)

This compound was isolated as yellowish white solid (95 mg, 58%): mp 189-192° C. $^1$H NMR (500 MHz, CDCl$_3$) δ 9.19 (s, 1H), 7.90 (s, 1H), 7.72 (s, 1H), 7.48 (d, J=3.7 Hz, 1H), 6.78 (d, J=3.7 Hz, 1H), 5.84 (s, 2H), 5.13 (t, J=11.7 Hz, 1H), 4.47 (m, 2H), 4.16 (s, 3H), 4.10 (s, 3H), 3.71-3.62 (m, 2H), 3.26-3.16 (m, 2H), 2.98 (s, 2H), 1.95 (s, 2H), 1.57 (s, 9H), 1.05-0.95 (m, 2H), 0.05--0.01 (m, 9H); HRESIMS m/z calcd for $C_{32}H_{44}N_4O_6Si$ (MH)$^+$ 609.3102, found 609.3102.

tert-Butyl (R)-3-(7,8-Dimethoxy-5-oxo-1-((2-(trimethylsilyl)ethoxy)methyl)-1,5-dihydro-4H-benzo[c]pyrrolo[2,3-h][1,6]naphthyridin-4-yl)pyrrolidine 1-Carboxylate (16g)

This compound was isolated as a creamy white solid (95 mg, 60%): mp 156-158° C. $^1$H NMR (500 MHz, CDCl$_3$) δ 9.20 (s, 1H), 7.91 (s, 1H), 7.73 (s, 1H), 7.50 (s, 1H), 6.88 (s, 1H), 5.84 (s, 2H), 4.17 (s, 3H), 4.10 (s, 3H), 4.02 (s, 1H), 3.91 (s, 1H), 3.70 (s, 1H), 3.67-3.62 (m, 2H), 3.06 (s, 1H), 2.44 (s, 1H), 1.56 (s, 9H), 1.05-0.96 (m, 2H), 0.02 (s, 9H); HRESIMS m/z calcd for $C_{31}H_{42}N_4O_6Si$ (MH)$^+$ 595.2946, found 595.2949.

tert-Butyl (R)-3-(7,8-Dimethoxy-5-oxo-1-((2-(trimethylsilyl)ethoxy)methyl)-1,5-dihydro-4H-benzo[c]pyrrolo[2,3-h][1,6]naphthyridin-4-yl)piperidine 1-Carboxylate (16h)

This compound was isolated as a yellowish solid (82 mg, 52%): mp 148-152° C. $^1$H NMR (300 MHz, CDCl$_3$) δ 9.13 (s, 1H), 7.82 (s, 1H), 7.64 (s, 1H), 7.40 (d, J=3.7 Hz, 1H), 7.00-6.92 (m, 1H), 5.81 (s, 2H), 4.95 (m, 1H), 4.53-4.41 (m, 1H), 4.25 (s, 1H), 4.11 (s, 3H), 4.03 (s, 3H), 3.66-3.56 (m, 2H), 3.05 (m, 1H), 2.92-2.79 (m, 2H), 2.05 (s, 1H), 1.89 (s, 2H), 1.65 (s, 9H), 1.49 (s, 7H), 1.26 (t, J=7.2 Hz, 2H), 0.99-0.89 (m, 1H), -0.04 (s, 9H); HRESIMS m/z calcd for $C_{32}H_{44}N_4O_6Si$ (MH)$^+$ 609.3102, found 609.3104.

Methyl (R)-2-(7,8-dimethoxy-5-oxo-1-((2-(trimethylsilyl)ethoxy)methyl)-1,5-dihydro-4H-benzo[c]pyrrolo[2,3-h][1,6]naphthyridin-4-yl)-3-methylbutanoate (16i)

This compound was isolated as a yellow powder (0.1 g, 76%): mp 212-214° C. $^1$H NMR (500 MHz, CDCl$_3$) δ 9.27 (s, 1H), 7.91 (s, 1H), 7.78 (s, 1H), 7.49 (d, J=3.8 Hz, 1H), 6.95 (d, J=3.8 Hz, 1H), 5.83 (t, J=7.1 Hz, 2H), 5.51 (d, J=9.3 Hz, 1H), 4.18 (s, 3H), 4.09 (s, 3H), 3.76 (s, 3H), 3.71-3.62 (m, 2H), 3.26 (dd, J=16.0, 6.8 Hz, 1H), 1.49 (d, J=6.6 Hz, 3H), 1.35-1.26 (m, 1H), 1.04-0.93 (m, 2H), 0.78 (d, J=7.1 Hz, 3H), 0.06--0.01 (s, 9H); HRESIMS m/z calcd for $C_{28}H_{37}N_3O_6Si$ (MH)$^+$ 540.2524, found 540.2524.

Methyl (S)-2-(7,8-dimethoxy-5-oxo-1-((2-(trimethylsilyl)ethoxy)methyl)-1,5-dihydro-4H-benzo[c]pyrrolo[2,3-h][1,6]naphthyridin-4-yl)-3-methylbutanoate (16j)

This compound was isolated as a yellowish solid (91 mg, 63%): mp 208-210° C. $^1$H NMR (500 MHz, CDCl$_3$) δ 9.27 (s, 1H), 7.92 (s, 1H), 7.78 (s, 1H), 7.48 (d, J=3.7 Hz, 1H), 6.94 (d, J=3.8 Hz, 1H), 5.82 (t, J=6.7 Hz, 2H), 5.51 (d, J=9.3 Hz, 1H), 4.17 (s, 3H), 4.08 (s, 3H), 3.76 (d, J=6.7 Hz, 3H), 3.72-3.64 (m, 2H), 3.26 (dd, J=16.0, 6.8 Hz, 1H), 2.17 (s, 1H), 1.49 (d, J=6.6 Hz, 3H), 1.03-0.95 (m, 2H), 0.78 (d, J=7.1 Hz, 3H), 0.02 (s, 9H); HRESIMS m/z calcd for $C_{28}H_{37}N_3O_6Si$ (MH)$^+$ 540.2524, found 540.2524.

Methyl (R)-2-(7,8-Dimethoxy-5-oxo-1-((2-(trimethylsilyl)ethoxy)methyl)-1,5-dihydro-4H-benzo[c]pyrrolo[2,3-h][1,6]naphthyridin-4-yl)butanoate (16k)

This compound was isolated as a yellowish powder (0.1 g, 68%): mp 189-193° C. $^1$H NMR (500 MHz, CDCl$_3$) δ 9.19 (s, 1H), 7.85 (s, 1H), 7.71 (s, 1H), 7.42 (d, J=3.6 Hz, 1H), 6.81 (d, J=3.6 Hz, 1H), 5.80-5.72 (m, 2H), 5.65 (t, J=7.2 Hz, 1H), 4.13 (s, 3H), 4.04 (s, 3H), 3.74 (s, 3H), 3.62-3.55 (m, 2H), 2.61 (dt, J=14.8, 7.4 Hz, 1H), 2.39 (dt, J=14.6, 7.3 Hz, 1H), 1.00 (t, J=7.5 Hz, 3H), 0.95-0.89 (m, 2H), -0.05 (s, 9H); HRESIMS m/z calcd for $C_{27}H_{35}N_3O_6Si$ (MH)$^+$ 526.2368, found 526.2370.

Methyl (S)-2-(7,8-Dimethoxy-5-oxo-1-((2-(trimethylsilyl)ethoxy)methyl)-1,5-dihydro-4H-benzo[c]pyrrolo[2,3-h][1,6]naphthyridin-4-yl)butanoate (16l)

This compound was isolated as a yellowish solid (0.072 g, 55%): mp 188-192° C. $^1$H NMR (500 MHz, CDCl$_3$) δ 9.19 (s, 1H), 7.85 (s, 1H), 7.71 (s, 1H), 7.42 (d, J=3.6 Hz, 1H), 6.81 (d, J=3.6 Hz, 1H), 5.80-5.72 (m, 2H), 5.65 (t, J=7.2 Hz, 1H), 4.13-4.08 (m, 4H), 4.04 (d, J=13.7 Hz, 3H), 3.74 (s, 3H), 3.62-3.55 (m, 2H), 2.61 (dt, J=14.8, 7.4 Hz, 1H), 2.39 (dt, J=14.6, 7.3 Hz, 1H), 1.00 (t, J=7.5 Hz, 3H), 0.95-0.89 (m, 2H), -0.05 (s, 9H); HRESIMS m/z calcd for $C_{27}H_{35}N_3O_6Si$ (MH)$^+$ 526.2368, found 526.2370.

General Procedure for the Deprotection of the SEM Group (Compounds 17a-j)

Compounds 16a-j (0.1 mmol) were dissolved in methylene chloride (2 mL) and TFA (2 mL) was added to the solution dropwise. The mixture was stirred at room temperature for 2 h and then the solvent was evaporated. The residue was dissolved in MeOH (5 mL) and ethylenediamine (1 mL) was added and the mixture was stirred overnight at 50° C. The mixture was acidified with TFA and extracted with CHCl$_3$ (3×10 mL). The combined organic layer was washed with water and brine (15 mL each), dried and evaporated to yield 17a-j as white solids.

4-Cyclohexyl-7,8-dimethoxy-1,4-dihydro-5H-benzo[c]pyrrolo[2,3-h][1,6]naphthyridin-5-one (17a)

This compound was isolated as a white solid (28 mg, 74%): mp 233-235° C. IR (thin film) 3120, 3002. 2922, 2847, 1654, 1608, 1576, 1509, 1462, 1450, 1417, 1400, 1378, 1357, 1300, 1224, 1207, 1180, 1124, 1040 cm$^{-1}$; $^1$H NMR (500 MHz, DMSO) δ 12.08 (s, 1H), 9.30 (s, 1H), 7.95 (s, 1H), 7.64 (s, 1H), 7.54-7.45 (m, 1H), 6.58 (s, 1H), 4.85 (s, 1H), 3.99 (s, 3H), 3.85 (s, 3H), 2.85-2.71 (m, 2H), 1.85 (d, J=11.6 Hz, 4H), 1.71 (d, J=11.1 Hz, 1H), 1.42 (d, J=13.2 Hz, 2H), 1.23 (m, 2H); MALDIMS m/z (rel intensity) 378 (MH)$^+$; HRESIMS calcd for C$_{22}$H$_{23}$N$_3$O$_3$ (MH)$^+$ 378.1812, found 378.1814; C18 HPLC purity, 100% (MeOH—H$_2$O, 85:15).

4-(Cyclohexylmethyl)-7,8-dimethoxy-1,4-dihydro-5H-benzo[c]pyrrolo[2,3-h][1,6]naphthyridin-5-one (17b)

This compound was isolated as a white solid (32 mg, 82%): mp 198-199° C. IR (thin film) 3314, 2922, 2849, 1654, 1634, 1573, 1511, 1463, 1450, 1422, 1358, 1385, 1325, 1259, 1206, 1124, 1178, 1051, 1009 cm$^{-1}$; $^1$H NMR (300 MHz, DMSO) δ 12.09 (s, 1H), 9.38 (s, 1H), 8.31 (s, 1H), 8.02 (s, 1H), 7.72 (s, 1H), 7.54 (s, 1H), 6.76 (s, 1H), 4.61 (s, 2H), 4.03 (s, 3H), 3.89 (s, 3H), 1.8 (m, 1H), 1.62 (m, 5H), 1.25-0.94 (m, 6H); MALDIMS m/z (rel intensity) 392 (MH)$^+$; HRESIMS calcd for C$_{23}$H$_{25}$N$_3$O$_3$ (MH)$^+$ 392.1969, found 392.1968; C18 HPLC purity, 97.15% (MeOH—H$_2$O, 85:15).

4-Cycloheptyl-7,8-dimethoxy-1,4-dihydro-5H-benzo[c]pyrrolo[2,3-h][1,6]naphthyridin-5-one (17c)

This compound was isolated as a white solid (35 mg, 89%): mp 242-244° C. IR (thin film) 3120, 2926, 2849, 1651, 1610, 1576, 1508, 1462, 1449, 1397, 1356, 1310, 1240, 1258, 1208, 1175, 1120, 1069 cm$^{-1}$; $^1$H NMR (500 MHz, DMSO) δ 12.15 (s, 1H), 9.38 (s, 1H), 8.02 (s, 1H), 7.71 (s, 1H), 7.57 (dd, J=10.7, 7.4 Hz, 1H), 6.75 (s, 1H), 5.17 (s, 1H), 4.05 (s, 3H), 3.92 (s, 3H), 2.85-2.63 (m, 2H), 1.96 (m, 4H), 1.71-1.54 (m, 6H), 1.25 (s, 3H); MALDIMS m/z (rel intensity) 392 (MH)$^+$; HRESIMS calcd for C$_{23}$H$_{25}$N$_3$O$_3$ (MH)$^+$ 392.1969, found 392.1969; C18 HPLC purity, 96.89% (MeOH—H$_2$O, 85:15).

4-Cyclooctyl-7,8-dimethoxy-1,4-dihydro-5H-benzo[c]pyrrolo[2,3-h][1,6]naphthyridin-5-one (17d)

This compound was isolated as a white solid (32 mg, 79%): mp 235-238° C. IR (thin film) 2918, 1644, 1607, 1571, 1510, 1463, 1416, 1378, 1354, 1334, 1263, 1241, 1207, 1180, 1164, 1062 cm$^{-1}$; $^1$H NMR (500 MHz, DMSO) δ 12.16 (s, 1H), 9.38 (s, 1H), 8.02 (s, 1H), 7.71 (s, 1H), 7.60 (s, 1H), 6.75 (s, 1H), 5.18 (s, 1H), 4.05 (s, 3H), 3.92 (s, 3H), 2.78 (d, J=11.5 Hz, 2H), 1.98-1.83 (m, 4H), 1.75 (m, 2H), 1.58 (m, 5H), 1.25 (m, 2H); MALDIMS m/z (rel intensity) 406 (MH)$^+$; HRESIMS calcd for C$_{24}$H$_{27}$N$_3$O$_3$ (MH)$^+$ 406.2125, found 406.2127; C18 HPLC purity, 96.27% (MeOH—H$_2$O, 85:15).

7,8-Dimethoxy-4-(1-methylpiperidin-4-yl)-1,4-dihydro-5H-benzo[c]pyrrolo[2,3-h][1,6]naphthyridin-5-one (17e)

This compound was isolated as a white solid (25 mg, 63%): mp 215-217° C. IR (thin film) 2936, 1633, 1607, 1569, 1512, 1463, 1418, 1353, 1334, 1309, 1258, 1231, 1185, 1143, 1125, 1037, 1011 cm$^{-1}$; $^1$H NMR (500 MHz, DMSO) δ 12.14 (s, 1H), 9.33 (s, 1H), 7.97 (s, 1H), 7.64 (s, 1H), 7.53 (d, J=3.4 Hz, 1H), 6.65 (s, 1H), 5.02 (m, 1H), 4.00 (s, 3H), 3.86 (s, 3H), 2.91 (m, 9H), 2.57-2.54 (m, 1H), 2.02-1.80 (m, 2H); MALDIMS m/z (rel intensity) 393 (MH)$^+$; HRESIMS calcd for C$_{22}$H$_{24}$N$_4$O$_3$ (MH)$^+$ 393.1921, found 393.1926; C18 HPLC purity, 99.09% (MeOH—H$_2$O, 85:15).

7,8-Dimethoxy-4-(piperidin-4-yl)-1,4-dihydro-5H-benzo[c]pyrrolo[2,3-h][1,6]naphthyridin-5-one (17f)

This compound was isolated as a white solid (18 mg, 47.5%): mp 258-259° C. IR (thin film) 2925, 1635, 1610, 1572, 1515, 1313, 1261, 1210, 1038 cm$^{-1}$; $^1$H NMR (500 MHz, DMSO) δ 12.07 (s, 1H), 9.31 (s, 1H), 7.95 (s, 1H), 7.64 (s, 1H), 7.51 (s, 1H), 6.61 (s, 1H), 4.92 (m, 1H), 3.99 (s, 3H), 3.86 (s, 3H), 3.12 (d, J=10.0 Hz, 3H), 2.89 (d, J=8.6 Hz, 2H), 2.61 (d, J=16.8 Hz, 4H), 1.73 (d, J=9.9 Hz, 2H); MALDIMS m/z (rel intensity) 379 (MH)$^+$; HRESIMS calcd for C$_{21}$H$_{22}$N$_4$O$_3$ (MH)$^+$ 379.1764, found 379.1762; C18 HPLC purity, 99.27% (MeOH—H$_2$O, 85:15).

(R)-7,8-Dimethoxy-4-(pyrrolidin-3-yl)-1,4-dihydro-5H-benzo[c]pyrrolo[2,3-h][1,6]naphthyridin-5-one (17g)

This compound was isolated as a white solid (10 mg, 27%): mp 274-276° C. IR (thin film) 2920, 1939, 1608, 1570, 1511, 1455, 1419, 1379, 1398, 1336, 1310, 1244, 1262, 1208, 1161, 1127, 1026 cm$^{-1}$; $^1$H NMR (500 MHz, DMSO) δ 12.16 (s, 1H), 9.39 (s, 1H), 8.04 (s, 1H), 7.72 (s, 1H), 7.58 (s, 1H), 6.96 (s, 1H), 5.72 (s, 1H), 4.06 (s, 3H), 3.92 (s, 3H), 3.26 (m, 2H), 2.99 (m, 1H), 2.30 (m, 2H), 0.88 (m, 1H); MALDIMS m/z (rel intensity) 365 (MH)$^+$; HRESIMS calcd for C$_{20}$H$_{20}$N$_4$O$_3$ (MH)$^+$ 365.1608, found 365.1610; C18 HPLC purity, 100% (MeOH—H$_2$O, 85:15).

(R)-7,8-Dimethoxy-4-(piperidin-3-yl)-1,4-dihydro-5H-benzo[c]pyrrolo[2,3-h][1,6]naphthyridin-5-one (17h)

This compound was isolated as a white solid (18 mg, 48%): mp 286-287° C. IR (thin film) 3130, 2919, 1649, 1610, 1577, 1509, 1463, 1407, 1378, 1334, 1310, 1242, 1209, 1175, 1127, 1022 cm$^{-1}$; $^1$H NMR (500 MHz, DMSO) δ 12.13 (s, 1H), 9.37 (s, 1H), 8.02 (s, 1H), 7.69 (s, 1H), 7.57 (s, 1H), 6.86 (s, 1H), 5.00 (m, 1H), 4.06 (s, 3H), 3.92 (s, 3H), 3.82 (t, J=11.0 Hz, 1H), 3.10 (d, J=11.3 Hz, 1H), 2.96 (d, J=18.6 Hz, 2H), 1.93-1.85 (m, 1H), 1.82 (s, 1H), 1.63 (d, J=13.3 Hz, 1H); MALDIMS m/z (rel intensity) 379 (MH)$^+$; HRESIMS calcd for C$_{21}$H$_{22}$N$_4$O$_3$ (MH)$^+$ 379.1764, found 379.1765; C18 HPLC purity, 99.29% (MeOH—H$_2$O, 85:15).

Methyl (R)-2-(7,8-Dimethoxy-5-oxo-1,5-dihydro-4H-benzo[c]pyrrolo[2,3-h][1,6]naphthyridin-4-yl)-3-methylbutanoate (17i)

This compound was isolated as a white solid (12 mg, 29%): mp 256-258° C. IR (thin film) 2922, 1726, 1608, 1572, 1514, 1461, 1420, 1386, 1334, 1268, 1184, 1137, 1021 cm$^{-1}$; $^1$H NMR (500 MHz, DMSO) δ 12.29 (s, 1H), 9.47 (s, 1H), 8.09 (s, 1H), 7.69 (s, 1H), 7.64-7.53 (m, 1H), 6.91 (s, 1H), 5.54 (d, J=9.3 Hz, 1H), 4.08 (s, 3H), 3.93 (s, 3H), 3.57 (s, 3H), 3.10-2.90 (m, 1H), 1.37 (d, J=6.6 Hz, 3H), 0.61 (d, J=7.1 Hz, 3H); MALDIMS m/z (rel intensity) 410 (MH)$^+$; HRESIMS calcd for $C_{22}H_{23}N_3O_5$ (MH)$^+$ 410.1711, found 410.1712; C18 HPLC purity, 100% (MeOH—H$_2$O, 85:15).

Methyl (S)-2-(7,8-dimethoxy-5-oxo-1,5-dihydro-4H-benzo[c]pyrrolo[2,3-h][1,6]naphthyridin-4-yl)-3-methylbutanoate (17j)

This compound was isolated as a white solid (26 mg, 68%): mp 274-276° C. IR (thin film) 2956, 1741, 1652, 1608, 1570, 1513, 1461, 1420, 1384, 1365, 1334, 1314, 1246, 1264, 1210, 1145, 1119, 1071, 1028 cm$^{-1}$; $^1$H NMR (500 MHz, DMSO) δ 12.21 (s, 1H), 9.40 (s, 1H), 8.03 (s, 1H), 7.63 (s, 1H), 7.57-7.47 (m, 1H), 6.85 (s, 1H), 5.48 (d, J=9.2 Hz, 1H), 4.02 (s, 3H), 3.87 (s, 3H), 3.51 (s, 3H), 3.01-2.91 (m, 1H), 1.31 (d, J=6.6 Hz, 3H), 0.55 (d, J=7.1 Hz, 3H); MALDIMS m/z (rel intensity) 410 (MH)$^+$; HRESIMS calcd for $C_{22}H_{23}N_3O_5$ (MH)$^+$ 410.1711, found 410.1710; C18 HPLC purity, 98.30% (MeOH—H$_2$O, 85:15).

(R)-2-(7,8-Dimethoxy-5-oxo-1,5-dihydro-4H-benzo[c]pyrrolo[2,3-h][1,6]naphthyridin-4-yl)butanoic Acid (17k)

Compound 16k (0.14 g, 0.226 mmol) was dissolved in methylene chloride (2 mL) and TFA (2 mL) was added to the solution dropwise. The mixture was stirred at room temperature for 2 h and then the solvent was evaporated. The residue was dissolved in MeOH (5 mL) and THF (5 mL) and ethylenediamine (1 mL) and NaOH (2 mL, 1 M soln) were added, and the mixture was stirred overnight at 60° C. The volatile solvents were removed and the solution was acidified with HCl to pH 3. The mixture was extracted with EtOAc (3×10 mL). The combined organic layer was washed with water and brine (15 mL each), dried and evaporated to yield 17k as a white solid (80 mg, 81%): mp 212-214° C. IR (thin film) 3262, 2921, 1722, 1657, 1608, 1574, 1463, 1422, 1387, 1338, 1314, 1264, 1246, 1211, 1137, 1082 cm$^{-1}$; $^1$H NMR (500 MHz, DMSO) δ 12.15 (s, 1H), 9.38 (s, 1H), 8.02 (s, 1H), 7.63 (s, 1H), 7.50 (s, 1H), 6.90 (s, 1H), 5.64 (s, 1H), 4.02 (s, 3H), 3.86 (s, 3H), 2.27 (m, 2H), 0.78 (t, J=7.5 Hz, 3H); MALDIMS m/z (rel intensity) 382 (MH)$^+$; HRESIMS calcd for $C_{20}H_{19}N_3O_5$ (MH)$^+$ 382.1397, found 382.1397.

(S)-2-(7,8-Dimethoxy-5-oxo-1,5-dihydro-4H-benzo[c]pyrrolo[2,3-h][1,6]naphthyridin-4-yl)butanoic acid (17l)

Following the same procedure used for 17k, compound 17l was isolated as a white solid (84 mg, 85%): mp 217-218° C. IR (thin film) 3544, 2937, 1704, 1676, 1601, 1515, 1459, 1425, 1390, 1330, 1310, 1264, 1229, 1211, 1181, 1147, 1028 cm$^{-1}$; $^1$H NMR (500 MHz, DMSO) δ 12.24 (s, 1H), 9.45 (s, 1H), 8.08 (s, 1H), 7.69 (s, 1H), 7.58 (s, 1H), 6.98 (s, 1H), 5.70 (s, 1H), 4.08 (s, 3H), 3.93 (s, 3H), 2.48-2.37 (m, 2H), 2.32 (d, J=6.6 Hz, 1H), 0.85 (t, J=7.5 Hz, 3H); MALDIMS m/z (rel intensity) 382 (MH)$^+$; HRESIMS calcd for $C_{20}H_{19}N_3O_5$ (MH)$^+$ 382.1397, found 382.1399.

(R)-2-(7,8-Dimethoxy-5-oxo-1-((2-(trimethylsilyl)ethoxy)methyl)-1,5-dihydro-4H-benzo[c]pyrrolo[2,3-h][1,6]naphthyridin-4-yl)-3-methylbutanoic acid (17m)

Compound 16i (0.1 mmol) was dissolved in methylene chloride (2 mL) and TFA (2 mL) was added to the solution dropwise. The mixture was stirred at room temperature for 2 h and then the solvent was evaporated. The residue was dissolved in MeOH (5 mL) and THF (5 mL) and ethylenediamine (1 mL) and NaOH (2 mL, 1 M soln) were added and the mixture was stirred overnight at 60° C. The volatile solvents were removed and the solution was acidified with HCl to pH 3. The mixture was extracted with EtOAc (3×10 mL). The combined organic layer was washed with water and brine (15 mL each), dried and evaporated to yield 17m as a yellow solid (0.11 g, 96%): mp 198-200° C. IR (thin film) 3513, 2968, 1720, 1665, 1606, 1514, 1459, 1442, 1388, 1329, 1264, 1183, 1136, 1017 cm$^{-1}$; $^1$H NMR (500 MHz, DMSO) δ 12.22 (s, 1H), 9.40 (s, 1H), 8.02 (s, 1H), 7.68 (m, 1H), 7.60-7.40 (m, 1H), 6.82 (s, 1H), 5.35 (d, J=9.3 Hz, 1H), 4.02 (s, 3H), 3.87 (s, 3H), 2.98 (dd, J=15.8, 6.9 Hz, 1H), 1.32 (d, J=8.6 Hz, 3H), 0.56 (d, J=7.1 Hz, 3H); MALDIMS m/z (rel intensity) 396 (MH)$^+$; HRESIMS calcd for $C_{21}H_{21}N_3O_5$ (MH)$^+$ 396.1554, found 396.1553.

(R)-3-(3-(7,8-Dimethoxy-5-oxo-1,5-dihydro-4H-benzo[c]pyrrolo[2,3-h][1,6]naphthyridin-4-yl)piperidin-1-yl)-3-oxopropanenitrile (18)

Compound 17h (30 mg, 0.08 mml) was added to a solution of HATU (30 mg, 0.08 mmol), DIPEA (30 mg 0.24 mmol) in and cyanoacetic acid (5 mg) in DMF (4 mL). The mixture was stirred at room temperature for 24 h and then quenched with saturated ammonium chloride (15 mL). The solution was extracted with EtOAc (3×15 mL). The combined organic layer was washed with saturated sodium bicarbonate (15 mL), water and brine and dried using anhydrous sodium sulfate. The residue obtained after evaporation of the organic layer was purified using column chromatography (CH$_2$Cl$_2$:MeOH 9.8:0.2) to give compound 18 as white solid (26 mg, 73%): mp 185-187° C. IR (thin film) 2928, 2262, 1645, 1608, 1573, 1512, 1446, 1417, 1378, 1333, 1308, 1261, 1208, 1129, 1063 cm$^{-1}$; $^1$H NMR (500 MHz, DMSO) δ 12.11 (d, J=18.0 Hz, 1H), 9.33 (s, 1H), 7.98 (s, 1H), 7.64 (d, J=4.1 Hz, 1H), 7.51 (d, J=12.7 Hz, 1H), 6.59 (m, 1H), 4.82 (s, 1H), 4.63 (d, J=11.5 Hz, 1H), 4.45 (d, J=11.2 Hz, 1H), 4.21 (d, J=19.0 Hz, 1H), 4.10 (d, J=18.9 Hz, 1H), 3.99 (s, 3H), 3.86 (s, 3H), 3.72 (d, J=14.4 Hz, 2H), 3.06 (t, J=12.1 Hz, 1H), 2.88 (m, 2H), 2.50 (s, 2H), 1.86 (m, 1H), 1.68 (m, 1H); MALDIMS m/z (rel intensity) 446 (MH)$^+$; HRESIMS calcd for $C_{24}H_{23}N_5O_4$ (MH)$^+$ 446.1823, found 446.1822; C18 HPLC purity, 95.85% (MeOH—H$_2$O, 85:15).

(R)-1-(2-(7,8-Dimethoxy-5-oxo-1,5-dihydro-4H-benzo[c]pyrrolo[2,3-h][1,6]naphthyridin-4-yl)-3-methylbutanoyl)azetidine-3-carbonitrile (19a)

Following the same procedure used for compound 18 and starting with 17m, compound 19a was isolated as a white solid (48 mg, 86%): mp 236-238° C. IR (thin film) 3248, 2965, 1649, 1608, 1570, 1514, 1413, 1367, 1332, 1264, 1210, 1138, 1115, 1022 cm$^{-1}$; $^1$H NMR (500 MHz, DMSO) δ 12.25 (s, 1H), 9.42 (s, 1H), 8.03 (s, 1H), 7.66 (s, 1H), 7.58 (s, 1H), 7.05-6.88 (m, 1H), 5.48 (s, 1H), 4.02 (s, 3H), 4.00-3.95 (m, 1H), 3.88 (s, 3H), 3.81 (m, 1H), 3.42 (m, 1H), 3.03 (m, 1H), 1.26 (d, J=6.6 Hz, 3H), 0.50 (d, J=7.2 Hz, 3H); MALDIMS m/z (rel intensity) 460 (MH)$^+$; HRESIMS calcd for $C_{25}H_{25}N_5O_4$ (MH)$^+$ 460.1979, found 460.1981; C18 HPLC purity, 100% (MeOH—H$_2$O, 85:15).

(R)-2-(7,8-Dimethoxy-5-oxo-1,5-dihydro-4H-benzo[c]pyrrolo[2,3-h][1,6]naphthyridin-4-yl)-3-methyl-N-(2,2,2-trifluoroethyl)butanamide (19b)

Following the same procedure used for compound 18 and starting with 17m, compound 19b was isolated as a white solid (45 mg, 74%): mp 247-248° C. IR (thin film) 3123, 2970, 2878, 1677, 1627, 1608, 1548, 1514, 1465, 1418, 1397, 1387, 1362, 1334, 1309, 1282, 1233, 1213, 1159, 1120, 1063 1034 cm$^{-1}$; $^1$H NMR (500 MHz, DMSO) δ 12.17 (s, 1H), 9.40 (s, 1H), 8.63 (t, J=6.3 Hz, 1H), 8.03 (s, 1H), 7.64 (s, 1H), 7.53 (s, 1H), 6.82 (s, 1H), 5.25 (d, J=9.5 Hz, 1H), 4.02 (s, 3H), 3.96 (m, 1H), 3.86 (s, 3H), 3.70 (m, 1H), 2.99 (m, 1H), 1.19 (d, J=6.5 Hz, 3H), 0.38 (d, J=6.8 Hz, 3H); MALDIMS m/z (rel intensity) 477 (MH)$^+$; HRESIMS calcd for $C_{23}H_{23}F_3N_4O_4$ (MH)$^+$ 477.1744, found 477.1744; C18 HPLC purity, 97.59% (MeOH—H$_2$O, 85:15).

(R)-1-(2-(7,8-Dimethoxy-5-oxo-1,5-dihydro-4H-benzo[c]pyrrolo[2,3-h][1,6]naphthyridin-4-yl)butanoyl)azetidine-3-carbonitrile (20a)

Compound 17k (30 mg, 0.08 mmol) was added to a solution of HATU (30 mg, 0.08 mmol) and DIPEA (30 mg 0.24 mmol) in DMF (4 mL). After stirring for 5 min, azetidine-3-carbonitrile hydrochloride (13 mg, 0.09 mmol) was added to the mixture. The mixture was stirred at room temperature for 24 h and then the reaction was quenched with saturated ammonium chloride (15 mL). The solution was extracted with EtOAc (3×15 mL). The combined organic layer was washed with saturated sodium bicarbonate (15 mL), water and brine and dried using anhydrous sodium sulfate. The residue obtained after evaporation of the organic layer was purified using silica gel column chromatography (CH$_2$Cl$_2$:MeOH 9.8:0.2) to give compound 20a as a white solid (28 mg, 60%): mp 257-260° C. IR (thin film) 3313, 2957, 1649, 1609, 1572, 1514, 1464, 1421, 1385, 1310, 1262, 1209, 1152, 1040 cm$^{-1}$; $^1$H NMR (500 MHz, DMSO) δ 12.26 (s, 1H), 9.47 (s, 1H), 8.09 (s, 1H), 7.72 (s, 1H), 7.62 (s, 1H), 7.06 (s, 1H), 5.77 (s, 1H), 4.08 (s, 3H), 3.99 (t, J=8.9 Hz, 1H), 3.94 (s, 3H), 3.88 (d, J=8.4 Hz, 1H), 3.54 (s, 1H), 2.47-2.36 (m, 2H), 2.21 (d, J=7.6 Hz, 1H), 0.81 (t, J=7.6 Hz, 3H); MALDIMS m/z (rel intensity) 446 (MH)$^+$; HRESIMS calcd for $C_{24}H_{23}N_5O_4$ (MH)$^+$ 446.1823, found 446.1828; C18 HPLC purity, 96.72% (MeOH—H$_2$O, 85:15).

(R)-2-(7,8-Dimethoxy-5-oxo-1,5-dihydro-4H-benzo[c]pyrrolo[2,3-h][1,6]naphthyridin-4-yl)-N-(2,2,2-trifluoroethyl)butanamide (20b)

Compound 17k (30 mg, 0.08 mmol) was added to a solution of HATU (30 mg, 0.08 mmol) and DIPEA (30 mg 0.24 mmol) in DMF (4 mL). After stirring for 5 min, trifluoroethylamine hydrochloride (11 mg, 0.09 mmol) was added to the mixture. The mixture was stirred at room temperature for 24 h and then quenched with saturated ammonium chloride (15 mL). The solution was extracted with EtOAc (3×15 mL). The combined organic layer was washed with saturated sodium bicarbonate (15 mL), water and brine and dried using anhydrous sodium sulfate. The residue obtained after evaporation of the organic layer was purified using silica gel column chromatography (CH$_2$Cl$_2$:MeOH 9.8:0.2) to give compound 20b as a white solid (20 mg, 55%): mp 267-268° C. IR (thin film) 3508, 2979, 2872, 2249, 1649, 1610, 1572, 1517, 1499, 1416, 1386, 1315, 1247, 1210, 1186, 1166, 1112, 1041 cm$^{-1}$; $^1$H NMR (500 MHz, DMSO-d$_6$) δ 12.10 (s, 1H), 9.37 (s, 1H), 8.50 (t, J=6.4 Hz, 1H), 8.02 (s, 1H), 7.62 (s, 1H), 7.49 (s, 1H), 6.64 (s, 1H), 5.56 (t, J=7.5 Hz, 1H), 4.01 (s, 3H), 3.86 (s, 3H), 3.64 (m, 2H), 2.65 (s, 1H), 2.32 (q, J=7.4 Hz, 2H), 0.52 (t, J=7.4 Hz, 3H); MALDIMS m/z (rel intensity) 463 (MH)$^+$; HRESIMS calcd for $C_{22}H_{21}F_3N_4O_4$ (MH)$^+$ 463.1588, found 463.1602; C18 HPLC purity, 98.86% (MeOH—H$_2$O, 85:15).

(S)-2-(7,8-Dimethoxy-5-oxo-1,5-dihydro-4H-benzo[c]pyrrolo[2,3-h][1,6]naphthyridin-4-yl)-N-(2,2,2-trifluoroethyl)butanamide (21)

Following the same procedure used for 20b but using the acid 17l, compound 21 was isolated as a white solid (24 mg, 60%): mp 235-237° C. IR (thin film) 3318, 2959, 1699, 1649, 1610, 1572, 1513, 1465, 1421, 1365, 1337, 1310, 1260, 1248, 1208, 1151, 1136 cm$^{-1}$; $^1$H NMR (500 MHz, DMSO-d$_6$) δ 12.16 (s, 1H), 9.43 (s, 1H), 8.56 (t, J=6.3 Hz, 1H), 8.08 (s, 1H), 7.68 (s, 1H), 7.58-7.52 (m, 1H), 6.70 (s, 1H), 5.62 (t, J=7.6 Hz, 1H), 4.08 (s, 3H), 4.07-3.99 (m, 1H), 3.92 (s, 3H), 3.71 (s, 2H), 2.39 (t, J=7.5 Hz, 3H), 0.59 (t, J=7.4 Hz, 3H); MALDIMS m/z (rel intensity) 463 (MH)$^+$; HRESIMS calcd for $C_{22}H_{21}F_3N_4O_4$ (MH)$^+$ 463.1588, found 463.1590; C18 HPLC purity, 100% (MeOH—H$_2$O, 85:15).

LIST OF ABBREVIATIONS

DCM Dichloromethane

DMA N,N-Dimethylacetamide

DMF N,N-Dimethylformamide

DMSO Dimethylsulphoxide

EtOAc Ethylacetate

HATU (1-[Bis(dimethylamino)methylene]-1H-1,2,3-triazolo[4,5-b]pyridinium 3-oxid hexafluorophosphate)

MOM Methoxymethyl

SEM 2-(Trimethylsilyl)ethoxymethyl

TEA Triethylamine

TFA Trifluoroacetic acid

THF Tetrahydrofurane

Those skilled in the art will recognize that numerous modifications can be made to the specific implementations described above. The implementations should not be limited to the particular limitations described. Other implementations may be possible.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

It is intended that that the scope of the present methods and compositions be defined by the following claims. However, it must be understood that this disclosure may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims.

What is claimed is:

1. A compound having the formula (I)

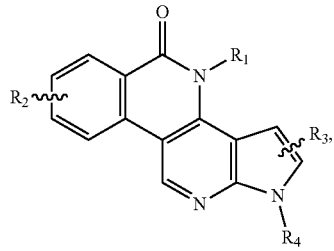

or a pharmaceutically acceptable salt, hydrate, or solvate thereof, wherein $R_1$ is an alkyl, alkenyl, heteroalkyl, heteroalkenyl, heterocyclyl, cycloalkyl, cycloalkenyl, cycloheteroalkyl, cycloheteroalkenyl, aryl, arylalkyl, and arylalkenyl, each of which is optionally substituted;

$R_2$ represent four substituents each independently selected from the group consisting of hydrogen, halo, azido, cyano, nitro, hydroxy, amino, thio, and derivatives thereof; or any two adjacent substituents that are taken together with the attached carbons to form an optionally substituted heterocycle, and each of other two substituents is defined as above;

$R_3$ represent two substituents each independently selected from the group consisting of hydrogen, halo, azido, cyano, nitro, hydroxy, amino, thio, and derivatives thereof; and $R_4$ is hydrogen, an alkyl, alkenyl, heteroalkyl, heteroalkenyl, heterocyclyl, cycloalkyl, cycloalkenyl, cycloheteroalkyl, cycloheteroalkenyl, aryl, arylalkyl, and arylalkenyl, each of which is optionally substituted.

2. The compound according to claim 1, wherein the compounds are:

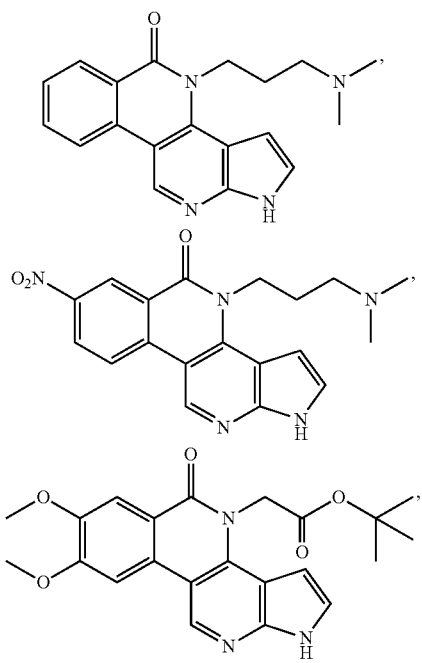

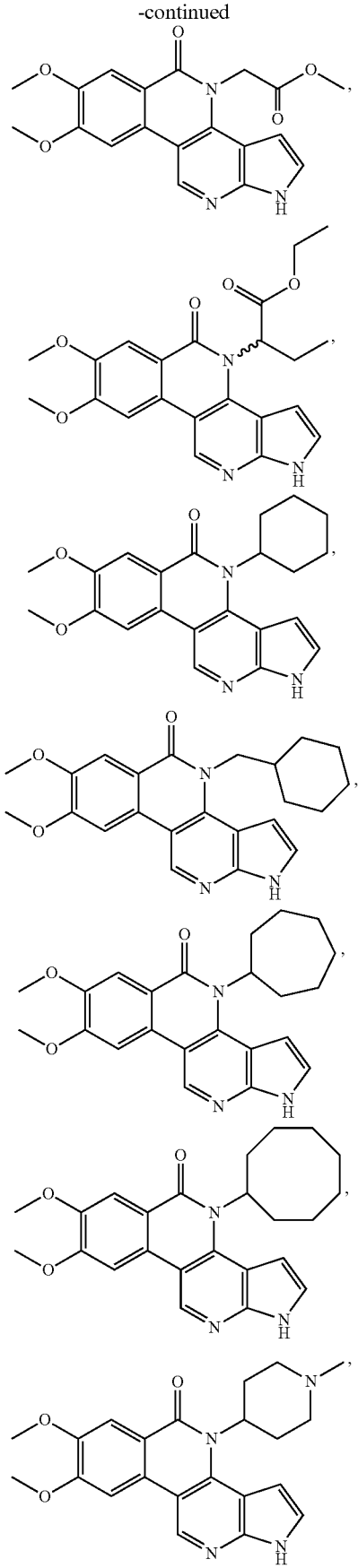

61
-continued

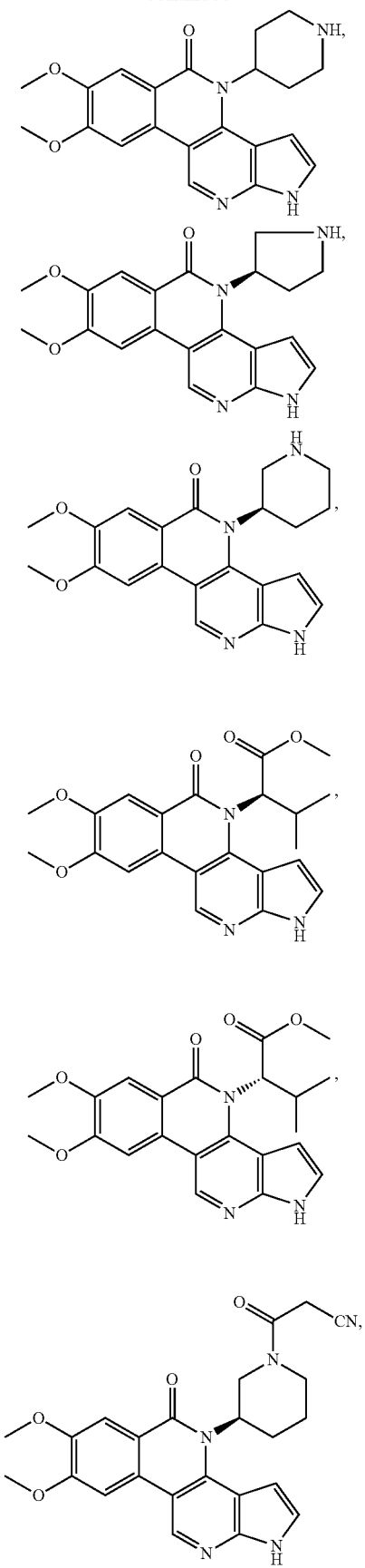

62
-continued

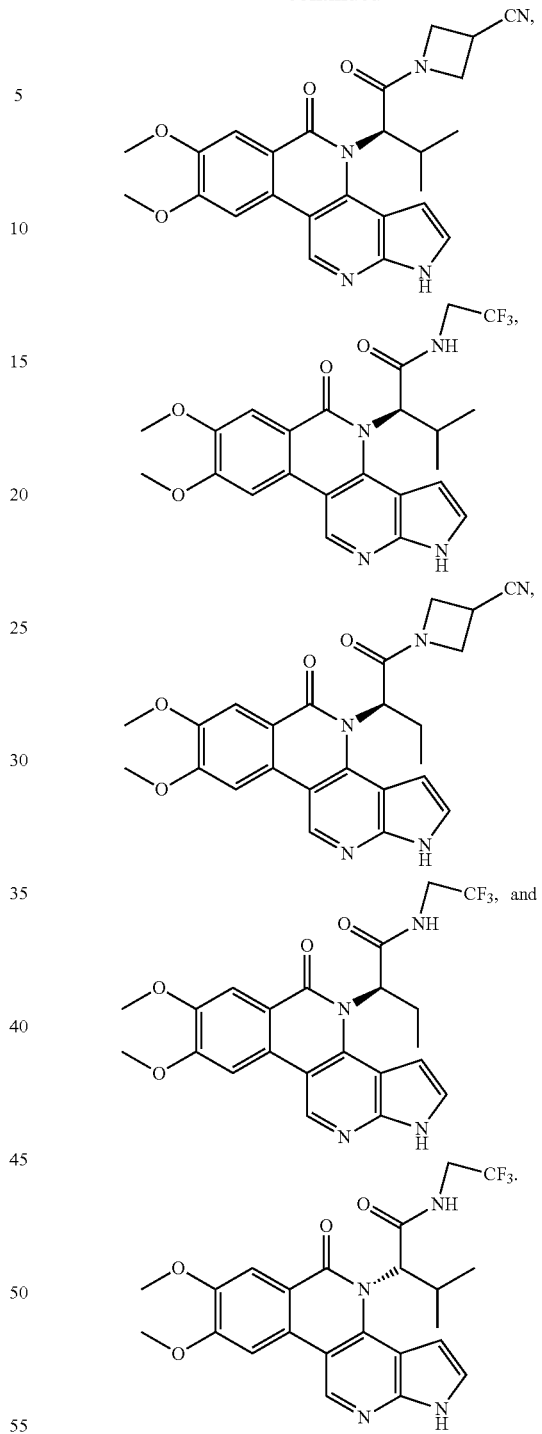

3. The compound according to claim 1, wherein $R_1$ is a C3-C8 alkyl, alkenyl, cycloalkyl, cycloalkenyl, and heterocyclyl, each of which is optionally substituted.

4. The compound according to claim 3, wherein $R_1$ is an optionally substituted C3-C8 cycloalkyl.

5. The compound according to claim 1, wherein $R_3$ and $R_4$ are hydrogen.

6. The compound according to claim 1, wherein the compound has the formula (II),

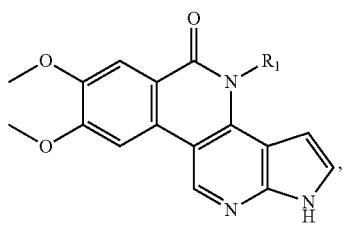

(II)

wherein R₁ is a C1-C12 alkyl, alkenyl, heteroalkyl, heteroalkenyl, heterocyclyl, cycloalkyl, cycloalkenyl, cycloheteroalkyl, cycloheteroalkenyl, aryl, arylalkyl, and arylalkenyl, each of which is optionally substituted.

7. The compound according to claim 6, wherein R₁ is a C3-C8 alkyl, alkenyl, cycloalkyl, cycloalkenyl, and heterocyclyl, each of which is optionally substituted.

8. The compound according to claim 7, wherein R₁ is an optionally substituted C3-C8 cycloalkyl.

9. The compound according to claim 6, wherein R₃ and R₄ are hydrogen.

10. The compound according to claim 6, wherein the compounds are:

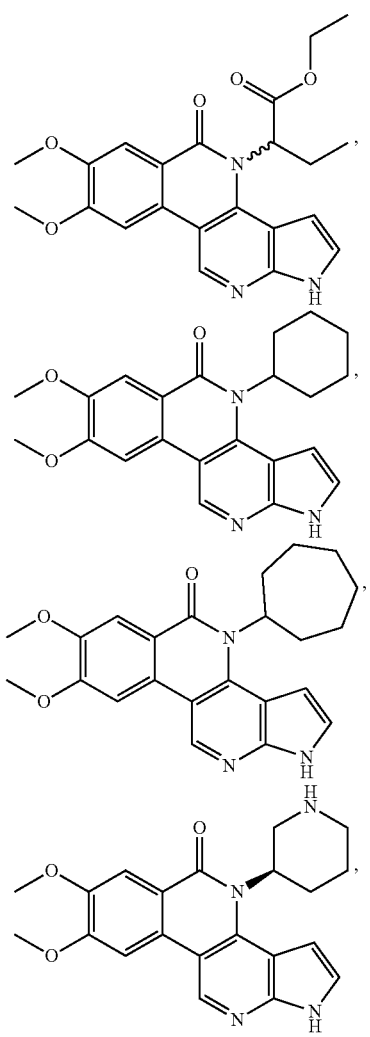

-continued

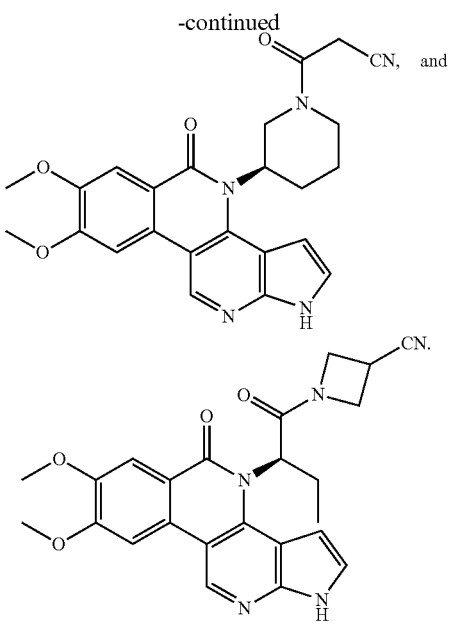

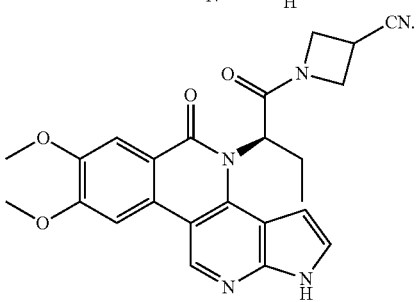

11. A pharmaceutical composition comprising one or more compounds of claim 1, or a pharmaceutically acceptable salt thereof, together with one or more diluents, excipients or carriers.

12. A pharmaceutical composition comprising one or more compounds of claim 1, or a pharmaceutically acceptable salt thereof, together with one or more diluents, excipients or carriers, for use in the treatment of a cancer, wherein said cancer comprises leukemia, non-small cell lung cancer (NSCLC), colon cancer, central neuro system (CNS) cancer, melanoma, ovarian cancer, renal cancer, prostate cancer and breast cancer.

13. A pharmaceutical composition comprising one or more compounds of claim 1, or a pharmaceutically acceptable salt thereof, and one or more other therapeutic compounds, together with one or more diluents, excipients or carriers, for use in the treatment of a cancer, wherein said cancer comprises leukemia, non-small cell lung cancer (NSCLC), colon cancer, central neuro system (CNS) cancer, melanoma, ovarian cancer, renal cancer, prostate cancer and breast cancer.

14. A method for treating a cancer, wherein said cancer comprises leukemia, non-small cell lung cancer (NSCLC), colon cancer, central neuro system (CNS) cancer, melanoma, ovarian cancer, renal cancer, prostate cancer and breast cancer, comprising the step of administering a therapeutically effective amount of one or more compounds of claim 1, and one or more carriers, diluents, or excipients, to a patient in need of relief from said cancer.

15. A method for treating a cancer, wherein said cancer comprises leukemia, non-small cell lung cancer (NSCLC), colon cancer, central neuro system (CNS) cancer, melanoma, ovarian cancer, renal cancer, prostate cancer and breast cancer, comprising the step of administering a therapeutically effective amount of a compound of claim 1 in combination with one or more other compounds of the same or different mode of action, and one or more carriers, diluents, or excipients, to a patient in need of relief from said cancer.

16. A method for treating diseases mediated by abnormal JAK/STAT signaling pathway, such as inflammation, cancer, viral and bacterial infections, neurological and immunological disorders, wherein said cancer comprises leukemia, non-small cell lung cancer (NSCLC), colon cancer, central neuro system (CNS) cancer, melanoma, ovarian cancer, renal cancer, prostate cancer and breast cancer, comprising the step of administering a therapeutically effective amount of one or more compounds of formula (I), and one or more carriers, diluents, or excipients, to a patient in need of relief from said disease:

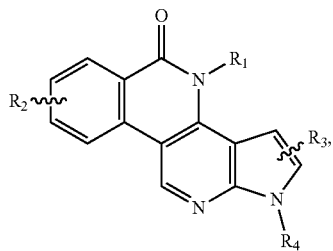

(I)

or a pharmaceutically acceptable salt, hydrate, or solvate thereof, wherein
R₁ is an alkyl, alkenyl, heteroalkyl, heteroalkenyl, heterocyclyl, cycloalkyl, cycloalkenyl, cyclohet- eroalkyl, cycloheteroalkenyl, aryl, arylalkyl, and arylalkenyl, each of which is optionally substituted;
R₂ represent four substituents each independently selected from the group consisting of hydrogen, halo, azido, cyano, nitro, hydroxy, amino, thio, and derivatives thereof; or any two adjacent substituents that are taken together with the attached carbons to form an optionally substituted heterocycle, and each of other two substituents is defined as above;
R₃ represent two substituents each independently selected from the group consisting of hydrogen, halo, azido, cyano, nitro, hydroxy, amino, thio, and derivatives thereof; and
R₄ is hydrogen, an alkyl, alkenyl, heteroalkyl, heteroalkenyl, heterocyclyl, cycloalkyl, cycloalkenyl, cycloheteroalkyl, cycloheteroalkenyl, aryl, arylalkyl, and arylalkenyl, each of which is optionally substituted.

17. The method according to claim 16, wherein R₁ is a C3-C8 alkyl, alkenyl, cycloalkyl, cycloalkenyl, and heterocyclyl, each of which is optionally substituted.

18. The method according to claim 16, wherein R₃ and R₄ are hydrogen.

* * * * *